United States Patent [19]
Hart et al.

[11] Patent Number: 5,954,732
[45] Date of Patent: Sep. 21, 1999

[54] SUTURING APPARATUS AND METHOD

[76] Inventors: Charles C. Hart, 8252 Mandeville, Huntington Beach, Calif. 92646; Brett Trauthen, 2021 Port Weybridge Pl., Newport Beach, Calif. 92692; Nabil Hilal, 24576 Vanessa Dr., Mission Viejo, Calif. 92691; Said Hilal, 25291 Spindlewood, Laguna Niguel, Calif. 92677; Bounsavanh Pravongviengkham, 450 Wilson Cir., Corona, Calif. 91719

[21] Appl. No.: 08/926,875

[22] Filed: Sep. 10, 1997

[51] Int. Cl.$^6$ ................................................ A61B 17/00
[52] U.S. Cl. .......................................... 606/144; 606/148
[58] Field of Search .................................. 606/144–148, 606/139, 232, 213, 158, 157, 222, 223; 112/169, 80.03; 604/168

[56] References Cited

U.S. PATENT DOCUMENTS

| | | | |
|---|---|---|---|
| 4,493,323 | 1/1985 | Albright et al. | 606/144 |
| 5,304,184 | 4/1994 | Hathaway et al. | 606/144 |
| 5,320,632 | 6/1994 | Heidmueller | 606/144 |
| 5,336,229 | 8/1994 | Noda | 606/144 |
| 5,336,231 | 8/1994 | Adair | 606/148 |
| 5,354,298 | 10/1994 | Lee et al. | 606/144 |
| 5,417,699 | 5/1995 | Klein et al. | 606/144 |
| 5,476,469 | 12/1995 | Hathaway et al. | 606/144 |
| 5,476,470 | 12/1995 | Fitzgibbons, Jr. | 606/144 |
| 5,527,321 | 6/1996 | Hinchliffe | 606/144 |
| 5,527,322 | 6/1996 | Klein et al. | 606/144 |
| 5,573,540 | 11/1996 | Yoon | 606/139 |
| 5,613,974 | 3/1997 | Andreas et al. | 606/144 |
| 5,700,273 | 12/1997 | Buelna et al. | 606/148 |
| 5,709,693 | 1/1998 | Taylor | 606/145 |
| 5,735,877 | 4/1998 | Pagedas | 607/421 |
| 5,792,152 | 8/1998 | Klein et al. | 606/213 |

FOREIGN PATENT DOCUMENTS

WO 97/03613  6/1997  WIPO .

*Primary Examiner*—Michael Buiz
*Assistant Examiner*—Vikki Trinh
*Attorney, Agent, or Firm*—Richard L. Myers

[57] ABSTRACT

A suturing apparatus adapted to close an incision and an anterior tissue wall includes an elongate support structure having an axis extending between a proximal end and distal end. A receiver disposed at the distal end is insertable through the incision in a low-profile state and expanded to a high-profile state on the far side of the tissue wall. Needles carried by the support structure are operable to extend through the support wall on either side of the incision and into the expanded receiver. Sutures advanced through the needles are captured by the receiver after the needles are removed and the receiver is returned to its low-profile state. Removal of the suturing apparatus from the incision draws the captured suture ends outwardly through the incision. A novel suture knot can be tied in the four suture ends and moved into proximity with the tissue wall to close the incision.

6 Claims, 22 Drawing Sheets

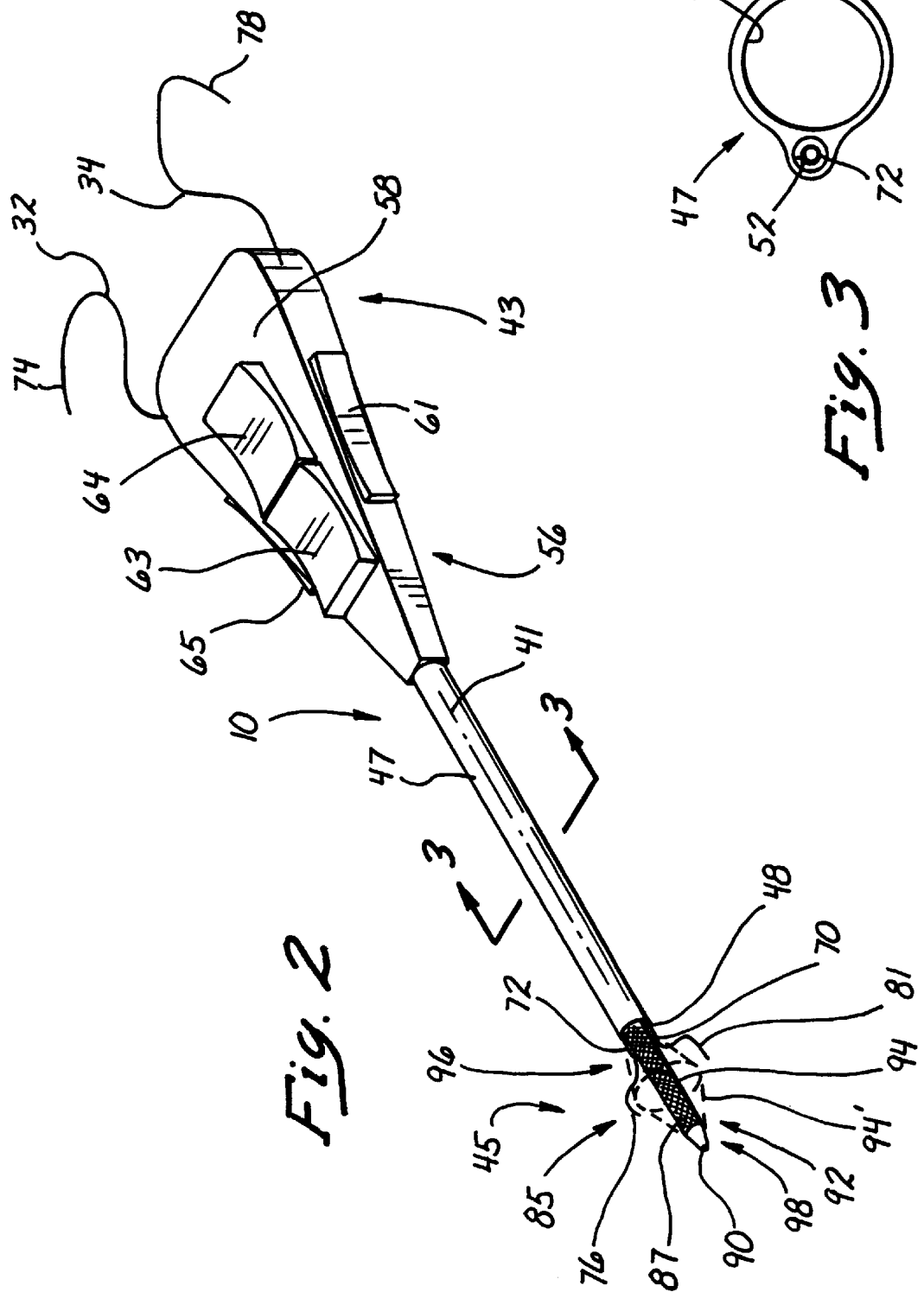

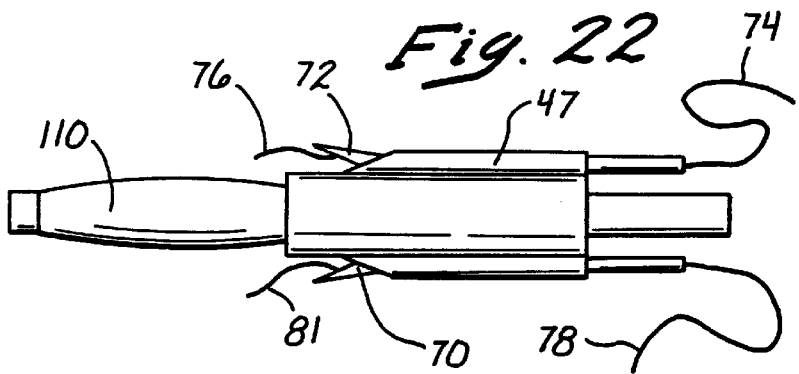
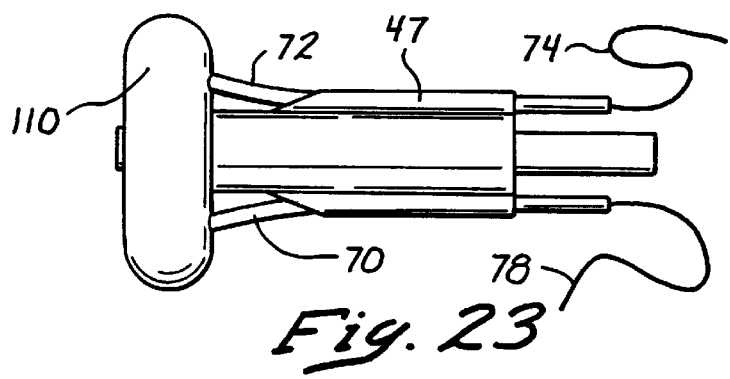
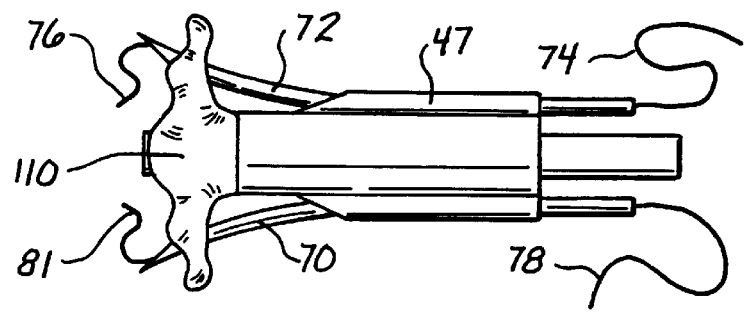
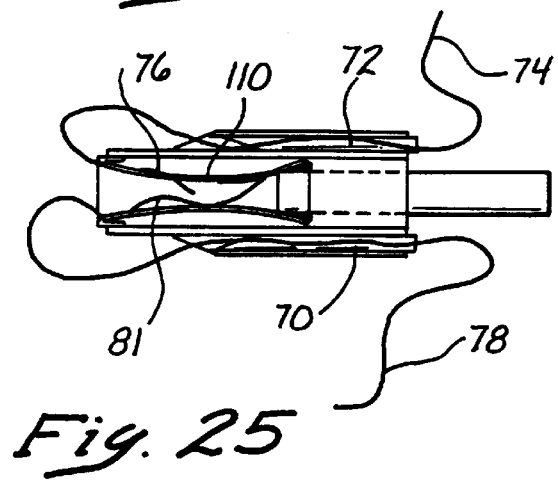

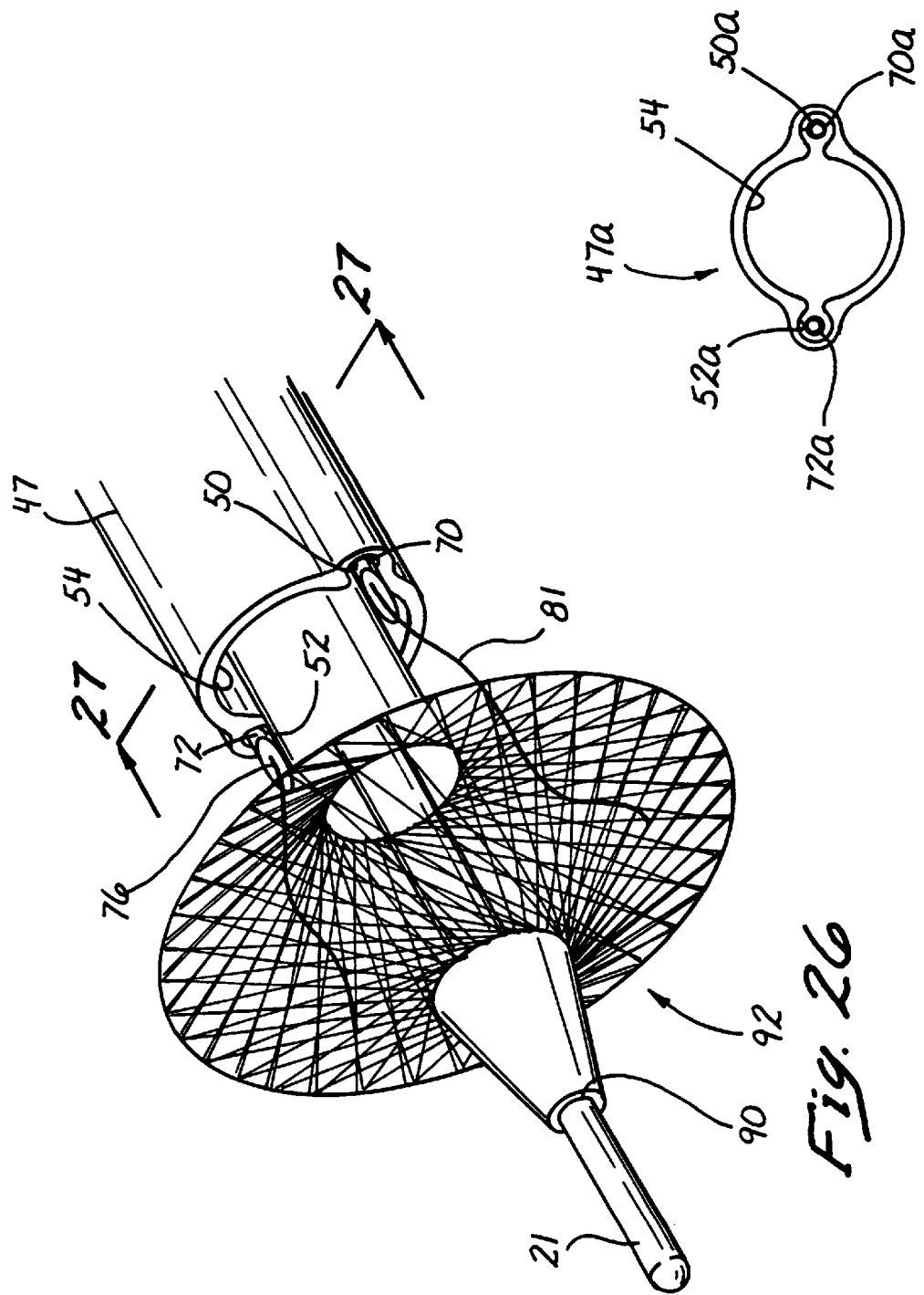

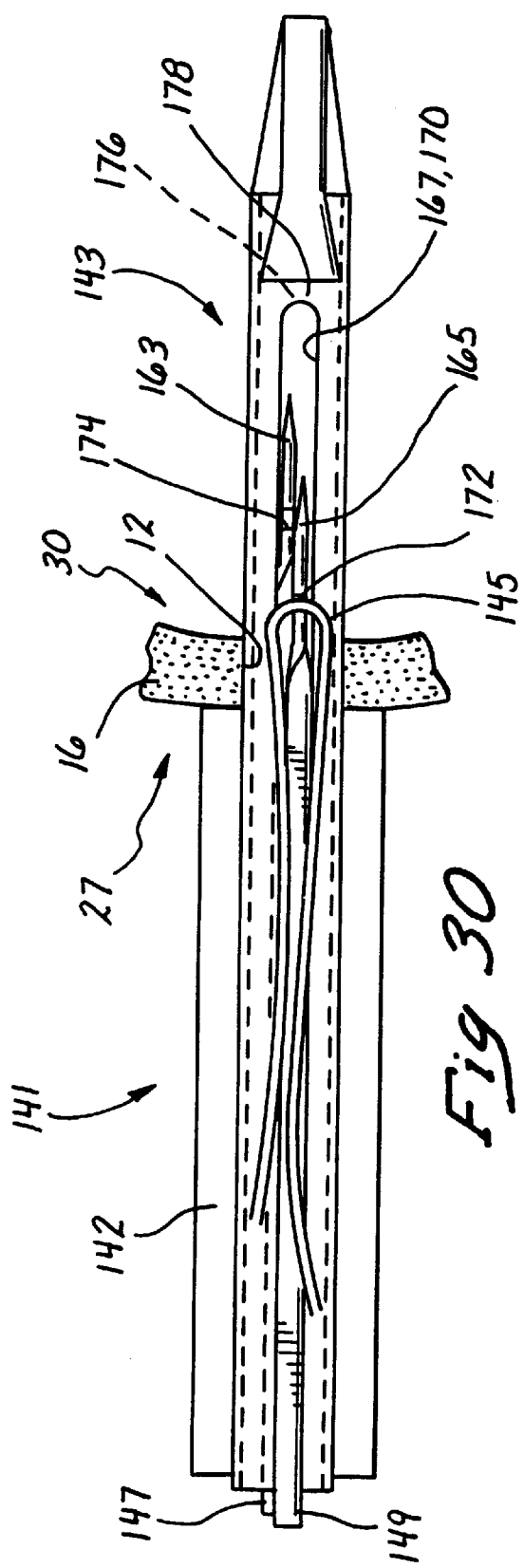
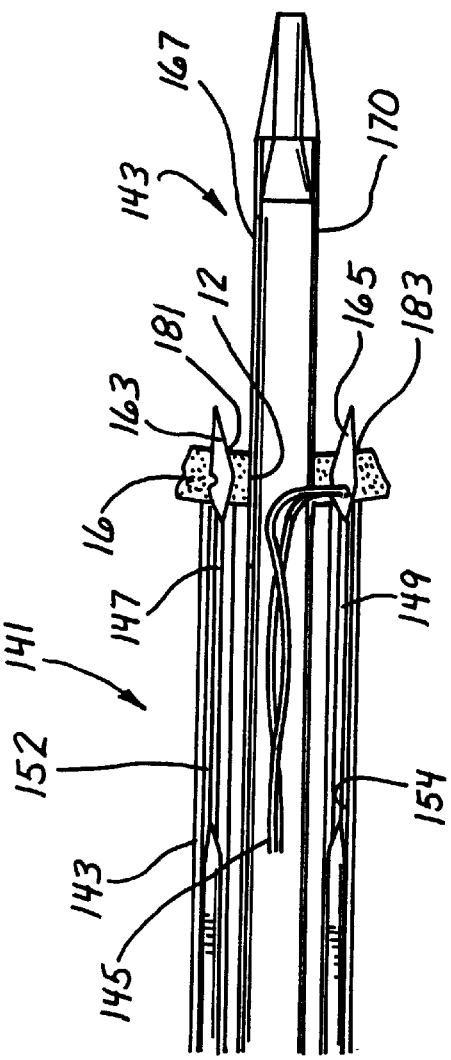

SUTURING APPARATUS AND METHOD

BACKGROUND AND FIELD OF THE INVENTION

This invention relates generally to suturing apparatus and methods and, more specifically, to such apparatus adapted for closing tissue wounds or incisions in a tissue wall.

DISCUSSION OF THE PRIOR ART

Wounds to tissue of the human body can occur accidentally or by way of an incision resulting from a surgical procedure. In either event, the tissue is pierced and the resulting incision or wound requires closure. The tissue will typically form a body wall having a near side and a far side with the incision or wound defined by surrounding tissue. The body wall will typically define a body cavity, such as the bladder, or a body conduit, such as a vessel. Small wounds or incisions, such as puncture sites, offer particular challenges since the far side of the body wall is not readily accessible for suturing.

The closure of a puncture, incision, or access site is desirable primarily to control bleeding. In the past, this bleeding has been addressed with manual or digital pressure applied externally to the site. Unfortunately, this procedure requires that the individual press on the site for an extended period of time. This requires the presence of another person in the surgical environment, but also can be very tiring to the individual applying pressure. Weights have also been applied to surgical sites to provide the pressure indicated. These weights do not benefit from the variable application of pressure which the individual can provide in the digital pressure technique previously discussed. Clips have been used to facilitate closure of wounds. These clips must ultimately be removed in a further step of the process. Plugs and adhesives have also been used but these typically leave some projection into the body cavity or conduit which tends to interfere with the natural flow of fluids. It can be seen that these present methods and materials are cumbersome, time-consuming, and potentially problematic.

An example of such a procedure might be the closure of an incision in the femoral artery or vein, the incision being initially made through a percutaneous site in order to facilitate the placement of a catheter. Closure of this incision in the interior blood vessel is complicated by the fact that the percutaneous incision is small and provides little opportunity for accessing the interior of blood vessel. Furthermore, the incision is in a vessel wall, the near side of which can be accessed, but the far side of which is generally inaccessible.

In the past, sutures have been placed by enlarging the percutaneous incision, and holding it open with graspers in order to view and access the interior vessel. Using a curved needle, the suture is placed by entering the near side of the vessel wall on one side of the incision, exiting the far side of that wall, entering the far side of the wall on the other side of the incision, and exiting that wall on the near side. Tying the two ends of the suture draws the opposing sides together, closing the wound or incision. This can be accomplished only with considerable trauma to the patient. The process is very difficult to perform in the limited space available and the resulting suture is often ineffective.

Suturing devices for closing of vascular puncture sites have also been disclosed as exemplified by U.S. Pat. No. 5,417,699, issued to Klein et al. This device comprises a shaft which carries an entire needle assembly through the incision to the far side of the wall. Needles are pulled proximally back through the surrounding tissue to facilitate closure of the wound. Unfortunately, this device sutures from the inside of the vessel and, therefore, requires that the bulk of the device initially be passed through the wound or incision to the far side of the vessel wall. Accordingly, this device is not capable of addressing small punctures or incisions.

SUMMARY OF THE INVENTION

These deficiencies of the prior art are overcome with the present invention which permits the blind or visually unassisted suturing of interior wounds or incisions. There is no need to enlarge the percutaneous incision, or otherwise use retractors in order to view and access the interior wall. Furthermore, there is no requirement for introducing an entire needle assembly through the incision to the far side of the wall in order to place the suture. Needle access need only be accommodated from the near side of the wall, which is more readily available. After the sutures are placed, the device can be removed through the percutaneous incision leaving multiple suture ends which can be tied with portions extending through the wound thereby facilitating a desirable abutting relationship between the sides of the incision.

The apparatus is particularly useful in closing an interior incision used for accessing an artery or vein with a catheter. Using the guidewire initially inserted to facilitate placement of the catheter, the device of this invention can be guided into the incision and the sutures placed blindly, without viewing the interior site.

In this context, access to the far side of the body wall (the vessel wall in this case) is extremely limited. Accordingly, preferred embodiments of the present invention typically include an elongate tube having an axis extending between a proximal end and a distal end. A receiver is disposed at the distal end of the tube and provided with a low-profile state facilitating its insertion through the wound or incision, and provided with a high-profile state to add structural support to the tissue on the far side of the body wall. The receiver may comprise an entanglement structure such as a woven or non-woven material or mesh. It may also comprise some other mass which might include an elastomeric material, foam, or some other metal or plastic suture-grasping mechanism. A suture is provided with a first end and a second end. Carriers in the form of needles are threaded with the first end of the suture and are operable to introduce the first end of the suture along a needle path from the near side to the far side of the body wall.

In preferred embodiments the receiver is expandable into the path of the needle on the far side of the body wall to engage and capture the first end of the suture. When the apparatus is withdrawn, the receiver pulls the first end of the suture back through the incision bringing the first end and the second end of the suture into proximity to facilitate knot tying. This apparatus is simple and inexpensive to manufacture. The low-profile state of the receiver makes the apparatus particularly suitable for small incisions such as punctures and access sites.

A two-needle embodiment of the invention provides four suture ends which facilitate tying of a novel suture knot wherein the first ends of each suture are tied to form a loop and the second ends of each suture are threaded through the loop from opposite directions and tied with a square knot. The resulting knot provides perfect alignment and an abutting relationship between the opposing edges of the surrounding tissue.

In one aspect of the invention, the suturing apparatus includes an elongate support structure having an axis extending between a proximal end and a distal end. A receiver disposed at the distal end is sized and configured to fit through the small incision and to provide structural support for the tissue on the far side of the body wall. One end of a suture is carried by a needle through the tissue surrounding the incision and into the receiver in an expanded state. The receiver has characteristics for capturing the suture end so that removal of the apparatus carries the suture end through the incision to facilitate tying of novel knot construction to close the incision.

In an associated method for closing the incision, the receiver is inserted through the incision from the near side of the body wall to the far side of the body wall. The first end of a suture is moved from the near side through the surrounding tissue and embedded in the receiver on the far side of the body wall. After the receiver captures the first end of the suture, it can be withdrawn from the far side of the wall through the incision bringing the first end of the suture exteriorly of the patient into proximity with the second end of the suture. A novel knot construction can then be tied to facilitate an abutting relationship between opposing edges of the incision.

In a further aspect of the invention the suturing device is adapted for closing a wound in body tissue having a near side and a far side. The device includes a shaft having an axis extending between a proximal end and a hollow distal end, the shaft being adapted for movement from the near side of the body tissue through the wound to the far side of the body tissue. A first stylet is operable from the proximal end of the shaft to carry a suture from the near side of the body tissue into the hollow distal end of the shaft. A second stylet, operable from the proximal end of the shaft, engages the suture within the hollow distal end of the shaft and moves the suture from the far side of the body tissue to the near side of the body tissue. The suture can then be tied on the near side of the body tissue to close the wound.

In another aspect of the invention, the first and second stylets are each extendable from a first position on the near side of the body tissue to a second position on the far side of the body tissue. The first stylet is operable from the proximal end of the shaft for carrying at least a portion of the suture between the first position and second position. The second stylet is operable from the proximal end of the shaft to engage the suture portion at the second position and to move the suture portion to the first position. The first and second stylets have a generally spaced relationship in the first position and a generally intersecting relationship at the second position.

In an additional aspect of the invention, the first stylet includes portions defining a hole sized and configured to receive the suture with the first stylet being operable to move the suture from the first position to the second position. The second stylet includes portions defining a hook sized and configured to engage the suture on the far side of the body wall and to withdraw the suture from the far side of the body wall to the near side of the body wall.

In a further aspect of the invention, the first stylet is movable along a first path to carry the suture from the near side of the body tissue to the far side of the body tissue. The second stylet is movable along a second path to engage the suture on the far side of the body tissue and to move the suture to the near side of the body tissue. At least one of the first path and the second path is curved on the far side of the body tissue.

In still a further aspect of the invention, an associated method includes the step of providing the hollow distal end of the shaft with first and second guide slots. The suture is attached to the first stylet on the near side of the body tissue and a portion of the suture moved by the first stylet to the far side of the body tissue. A second stylet is moved to the far side of the body tissue where it engages the suture portion. Moving the second stylet, and the engaged suture portion, from the far side to the near side of the body tissue, permits the tying of the suture to close the wound. Transfer of the suture portion from the first stylet to the second stylet can occur between the guide slots which may be opened or closed at the distal end of the shaft.

These and other features and advantages of the invention will become more apparent with a discussion of preferred embodiments and reference to the associated drawings.

DESCRIPTION OF THE DRAWINGS

FIG. 2 is an enlarged-perspective view of a preferred embodiment of the wound-closure apparatus of the present invention;

FIG. 3 is a radial cross-section view taken along lines 3—3 of FIG. 2.

FIG. 4 is a side elevation view illustrating the wound-closure apparatus with an elongate sheath, and a distal tip inserted through the incision;

FIG. 5 is a side elevation view similar to FIG. 4 and illustrating the distal tip in an advanced position;

FIG. 6 is a side elevation view similar to FIG. 5 and illustrating a suture-engagement mechanism in a deployed, high-profile state;

FIG. 7 is a side elevation view similar to FIG. 6 and illustrating the distal tip in a retracted position;

FIG. 8 is a side elevation view similar to FIG. 7 and illustrating the deployment of needles and sutures through the engagement mechanism;

FIG. 9 is a side elevation view similar to FIG. 8 and illustrating the engagement mechanism withdrawn into the sheath of the apparatus;

FIG. 10 is a side elevation view illustrating the apparatus removed from the patient leaving the sutures in place for tying;

FIG. 22 is a side elevation view of a further embodiment wherein the engagement mechanism is formed as a balloon;

FIG. 23 is a side elevation view similar to FIG. 22 wherein the engagement balloon is punctured by the needles into a collapsed state;

FIG. 24 is a side elevation view similar to FIG. 23 wherein the suture ends are captured in the collapsed balloon mechanism;

FIG. 25 is an axial cross-section view of the deflated balloon mechanism retracted with the suture ends captured in the mechanism;

FIG. 26 is a perspective view of a further embodiment of the sheath of the device wherein the needle lumens extend into the working channel of the sheath;

FIG. 27 is a radial cross-section view similar to FIG. 3 but taken along lines 27—27 of the embodiment of FIG. 26;

FIG. 29 through FIG. 37 relate to an additional embodiment of the invention, including a hollow shaft and a plurality of stylets;

FIG. 29 is a top plan view in axial cross-section of the additional embodiment;

FIG. 30 is a side-elevation view of the additional embodiment illustrating a pair of guide slots in the shaft;

FIG. 31 is a top plan view illustrating the hollow shaft extending through the wound and a pair of suture-manipulating stylets;

FIG. 32 is a top plan view illustrating one of the stylets in an advanced position;

FIG. 33 is a top plan view illustrating a second stylet in an advanced position permitting engagement of a suture by the first stylet;

FIG. 34 is a top plan view illustrating the second stylet being retracted with the suture engaged by the first stylet;

FIG. 35 is a top plan view illustrating the first stylet retracted along with the engaged portion of the suture;

FIG. 36 is a top plan view illustrating both stylets fully removed to a retracted position;

FIG. 37 is a top plan view illustrating withdrawal of the suturing device from the wound;

FIG. 38 is a top plan view of the further embodiment;

FIG. 39 is a side-elevation view further illustrating the open-ended guide slots in the shaft;

FIG. 41 is a top plan view of the stylet-operating mechanism prior to deployment of the stylet;

FIG. 42 is a top plan view of the stylet-operating mechanism when the first stylet is deployed to its advanced position;

FIG. 43 is a top plan view of the stylet-operating mechanism when the second stylet is deployed to its advanced position;

FIG. 44 is a top plan view of the stylet-operating mechanism with the second stylet withdrawn to its retracted position;

FIG. 45 is a top plan view illustrating the first stylet withdrawn to its retracted position;

FIG. 46 is a top plan view similar to FIG. 45 after deployment and withdrawal of the stylets;

DESCRIPTION OF PREFERRED EMBODIMENTS AND BEST MODE OF THE INVENTION

Figure 1:
FIG. 1 is a perspective view of a patient having an incision at an interior blood vessel, and a suturing apparatus of the present invention operable to close the resulting incision.

A suturing apparatus is illustrated in FIG. 1 and designated generally by the reference numeral 10. This apparatus 10 is particularly adapted for use in closing an interior wound or incision 12 of a patient 14. In FIG. 1, the incision 12 is made in a wall 16 of the femoral artery, vein, or other vessel 18 in preparation for the insertion of a catheter (not shown). Access to the interior vessel 18 is gained percutaneously through a cut 23 in the skin 25 of the patient 14.

In a manner well-known to those skilled in the art, the incision 12 is created in the wall 16 and a guidewire 21 is introduced into the vessel 18. This guidewire 21 facilitates insertion of the catheter (not shown) over the guidewire 21 and into the vessel 18. The present invention contemplates closure of the incision 12 after this primary procedure has been completed and the catheter removed.

In the illustrated example, the wall 16 of the vessel 18 is merely representative of any facial or tissue wall having a near side 27 and a far side 30, which may or may not require access through the skin 25 of the patient 14. The concept will be particularly appreciated in those situations where the far side 30 of the tissue wall, such as the vessel wall 16, is generally inaccessible.

With further reference to FIG. 1, it can be appreciated that the suture apparatus 10 is particularly adapted for the placement of sutures 32 and 34 around the incision 12. After the sutures 32, 34 are placed, the apparatus 10 can be removed from the patient 14 leaving the four ends of the sutures 32, 34 extending through the percutaneous cut 23. This can be accomplished without enlarging the percutaneous cut 23, without viewing the vessel 18, and without accessing the vessel wall 16 either from the near side 27, or the far side 30. A novel knot construction or bolster can be tied in the four ends of the sutures 32, 34 and slipped into position to close the incision 12.

A preferred embodiment of the suture apparatus 10 is illustrated in the enlarged views of FIGS. 2 and 3. From these views it can be seen that the apparatus 10 will typically have an elongate configuration and an axis 41 between a proximal end 43 and a distal end 45. A sheath 47, disposed at the proximal end of the apparatus 10, terminates in a distally-facing surface 48 and includes a pair of needle channels 50, 52 and a central working channel 54. A handle assembly 56 is disposed at the proximal end 43 of the apparatus 10 and includes a handle 58 and various triggers or finger tabs 61, 63, 64, and 65 which are movable thereon to operate the suture apparatus 10.

A pair of needles 70 and 72 are movable axially through the needle channels 50 and 52 by operation of the finger tabs 61 and 65, respectively. The suture 32, including suture ends 74 and 76, and the suture 34, including suture ends 78 and 81, are threaded through the respective needles 70 and 72. In this manner, the sutures 32, 34 extend through the apparatus 10 from the proximal end 43 to the distal end 45.

The needles 70, 72 are movable between proximal positions and distal positions by operation of the respective finger tabs 61 and 65. In the proximal position, the needles 70, 72 are disposed proximally of the sheath surface 48. In the distal position, the needles 70, 72 extend distally of the surface 48.

Of particular interest to the suture apparatus 10 is a suture engagement mechanism 85 which is movable within the working channel 54 between a proximal position and a distal position by operation of the finger tab 63. The engagement mechanism 85 in this particular embodiment includes a shaft, or a tube 87 having a through lumen 90. An expandable structure 92 is disposed around the tube 87 and is moveable by operation of the finger tab 64 between a radially-contracted, low-profile state illustrated by the solid lines 94 in FIG. 2, and a radially-expanded, high-profile state illustrated by the dotted lines 94' in FIG. 2. In this embodiment, the expandable structure 92 comprises a tubular mesh with a proximal end 96 fixed to the sheath 47 and a distal end 98 fixed to the tube 87. Initially, the expandable structure 92 is inserted through the wound 12 in a low-profile state. On the far side 30 of the wall 16, this structure 92 can be expanded and brought into contact with the wall 16. In this position, the expandable structure 92 provides support for the tissue wall 16. This support is particularly valuable in preventing distortion of the tissue wall 16 during penetration of the wall 16 by the needle 70, 72.

Given this general disclosure of a preferred embodiment of the suture apparatus 10, one can now refer to FIGS. 4–10 for a discussion of a method for using the apparatus 10. In a typical surgical operation, there may be many procedures involved. For example, a primary procedure might include the placement of a catheter through the cut 23 in the skin 25 and through the incision 12 into the femoral vessel 18. Since a catheter is not particularly steerable, its placement is usually preceded with the placement of the guidewire 21 which is snaked through the cut 23 and the incision 12 up to the operative site. The catheter is then moved over the guidewire 21 until it reaches the operative site. When this primary procedure has been completed, the catheter can be withdrawn.

At this point, the suture apparatus 10 of the present invention can be used to close the incision 12 in the vessel 18. A particular advantage in one aspect of this process involves the guidewire 21 which was initially used to guide the catheter in the primary procedure. With the guidewire 21 extending through the percutaneous cut 23 and the incision 12, the through-lumen 90 of the tube 87 can be threaded onto the guidewire 21 and the apparatus 10 moved along the guidewire 32 until the distal surface 48 of the sheath 47 contacts the vessel wall 16.

It will be noted that the suture apparatus 10 can be moved to this operative position merely following the guidewire 21. The vessel 18 need not be viewed through the cut 23 and no enlarged access through the cut 23 need be provided to accommodate needle thread and other suturing devices. The entire procedure associated with the suture apparatus 10 can be accomplished in this blind environment using the guidewire 21.

Figure 4:
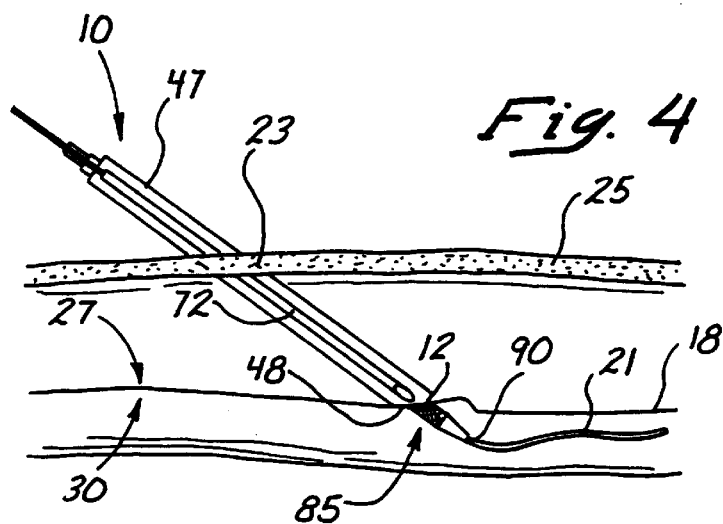
FIGS. 4–10 are a series of side-elevation views illustrating a method of wound closure associated with one embodiment of the present invention.

In FIG. 4, the suturing apparatus 10 is illustrated in its operative position along the guidewire 21. In this position, the suturing engagement mechanism 85 can be deployed by operation of the finger tab 63 on the proximal handle assembly 56. Moving this tab 63 in the distal direction forces the engagement mechanism 85 distally of the surface 48 and through the incision 12. Within the vessel 18, this engagement mechanism 85 continues to follow the guidewire 21 to the fully-extended state illustrated in FIG. 5.

Figure 6:
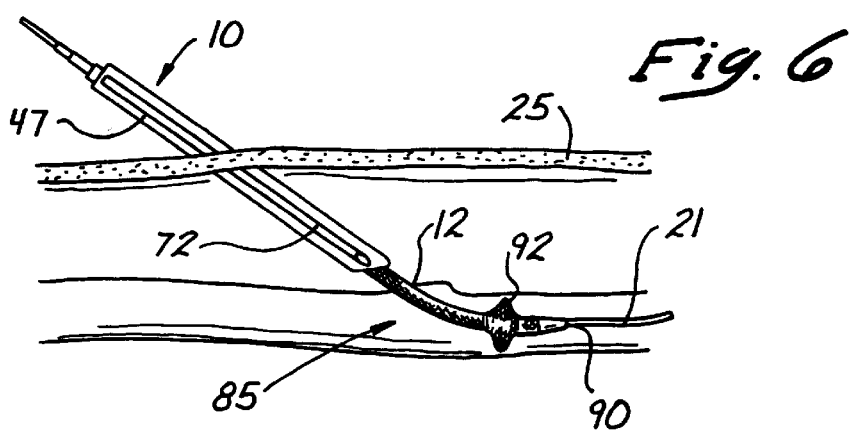

With the suture engagement mechanism 85 deployed in its fully-extended state, the expandable structure 92 can be moved from its low-profile state to its expanded or high-profile state, as illustrated in FIG. 6. This deployment of the expandable structure 92 is accomplished by operation of the finger tab 64 on the handle assembly 56.

Figure 7:
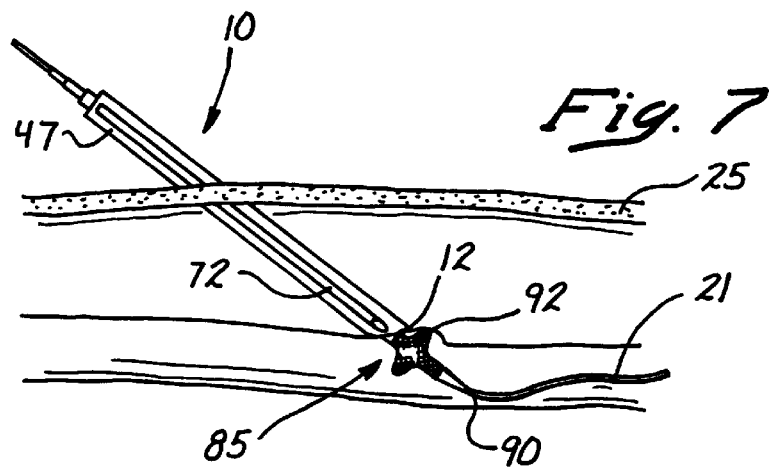

Drawing the suture engagement mechanism 85 proximally by operation of the finger tab 63 moves the expanded structure 92 against the far side 30 where it provides structural support for the vessel wall 16. This step in the process not only draws the expanded structure 92 against the far side 30 of the wall 16, but also moves the distally facing surface 48 of the sheath 47 against the near side 27 of the wall 16. Thus, the wall 16 is sandwiched between the surface 48 of the sheath 47 and the expanded structure 92, with the tube 87 of the mechanism 85 extending through the incision 12. This position of the suture apparatus 10 is illustrated in FIG. 7.

At this point, the needles 70, 72 can be moved distally within their respective needle channels 50, 52 so that they extend distally of the surface 48 and into the expanded structure 92 associated with the suturing engagement mechanism 85. This movement of the needle 70, 72 is accomplished by operation of the finger tabs 61 and 65, respectfully, and embeds the suture ends 81 and 76 in the expanded structure 92.

It will initially be noted that with the wall 16 sandwiched between the surface 48 and the expanded structure 92, the needles 70, 72 pass through the wall 16 on either side of the incision 12. It will also be noted that in order for the needles to extend into the expanded structure 92, this structure must be sufficiently radially expandable to extend into the path of the needles 70, 72. Since the sutures 32, 34 follow the path of the respective needles 70, 72, it follows that the sutures 32, 34 now extend through the percutaneous cut 23, through the wall 16 on either side of the incision 12, beyond the far side 30 of the wall 18, and into the expanded structure 92.

Figure 9:
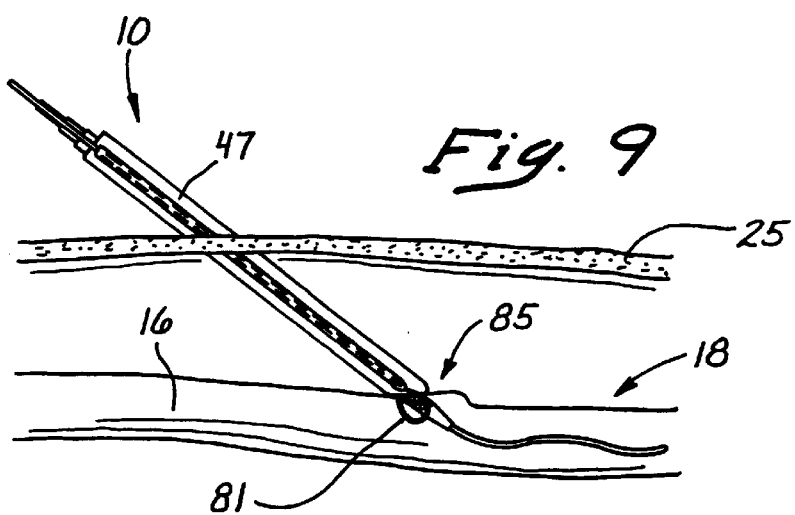

With the suture ends 76 and 81 embedded in the expanded structure 92, the entire suture apparatus 10 can be withdrawn from the operative site. This step may or may not be accompanied with a return of the expanded structure 92 to its low-profile state illustrated in the solid line of FIG. 2 and designated by the reference numeral 94. The removal of the apparatus 10 may or may not be preceded by a step for drawing the expandable structure 92, either in its low-profile or high-profile state, proximally back into the sheath 47 by operation of the finger tab 63. This step for moving the suture engagement mechanism 85 proximally into the sheath 47 is illustrated in FIG. 9.

Figure 10:
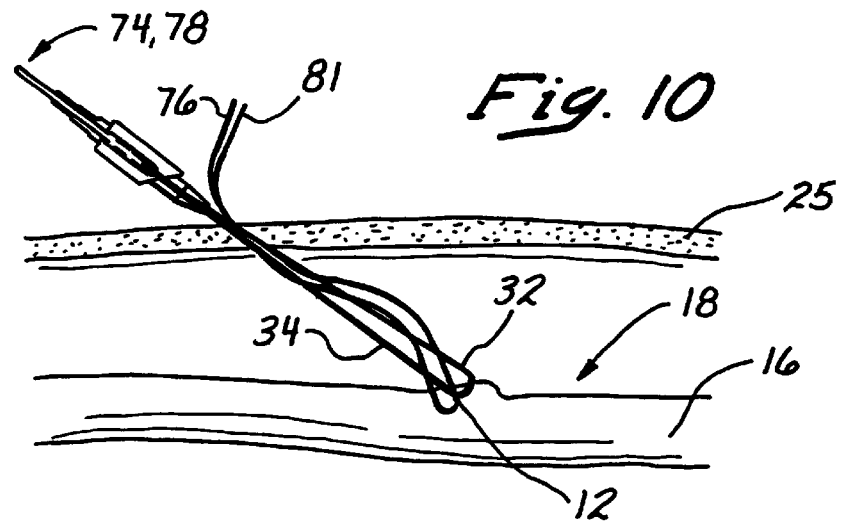
Figure 11:
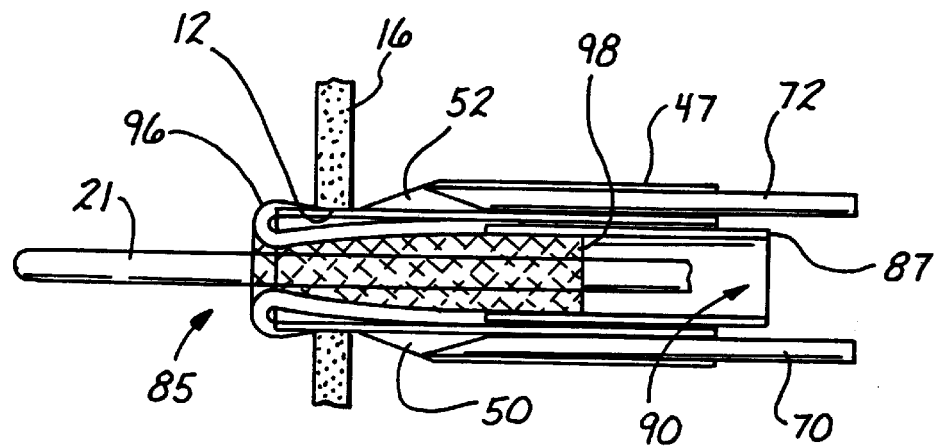
FIG. 11 is an axial view partially in section of a preferred embodiment of the apparatus prior to advancement and deployment of a mesh engagement mechanism.

The entire suture apparatus 10 is illustrated to be removed from the incision 12 and the percutaneous cut 23 in FIG. 10. At this point, it will be noted that all four ends 70, 72, 74, and 78 of the sutures 32 and 34 are disposed exteriorally of the patient 14. More importantly, the suture ends 74, 78 extend on opposite sides of the incision 12 from the near side 27 to the far side 30 of the wall 16. The ends 70, 72 of the sutures 32, 34 extend through the incision 12 from the far side 30 to the near side 27 of the wall 16.

Figure 5:
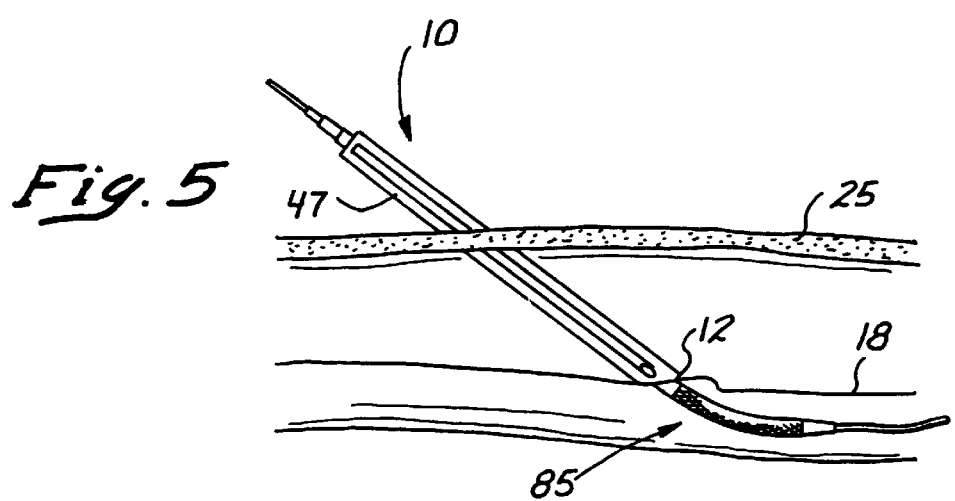

A more detailed description of the suture apparatus 10 is illustrated in FIGS. 11–15. This embodiment is similar in many respects to that previously described with reference to FIG. 2, except there is no finger tab 63 or movement of the suture engagement mechanism 85 to an extended position as illustrated in FIG. 5. Rather, the expandable structure 92 has its proximal end 96 attached directly to the sheath 47 and its distal end 98 attached directly to the inner sheath 47. When the apparatus 10 is placed over the guidewire 21, it is moved distally as previously discussed until the distal end of the sheath 47 and the proximal ends of the expandable structure 92 extend through the incision 12. At this point, the expandable structure 92 can be deployed by operation of the finger tab 94' to its high-profile state. With proper placement of the distal end of the sheath 47, this deployment of the expandable structure 92 will occur on the far side 30 of the wall 16. With the structure 92 thus expanded, the needles 70, 72 can be advanced within their channels 50, 52 by operation of the finger tabs 61, 65.

Figure 12:
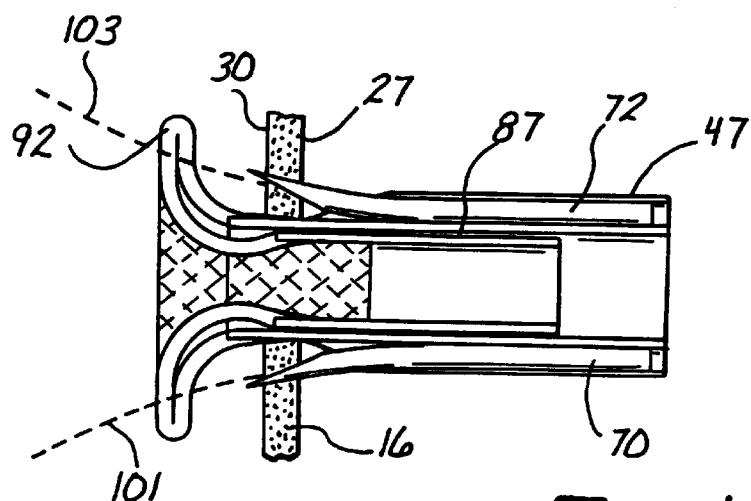
FIG. 12 is an axial cross-section view similar to FIG. 11 and illustrating the engagement mechanism in its deployed state.
Figure 13:
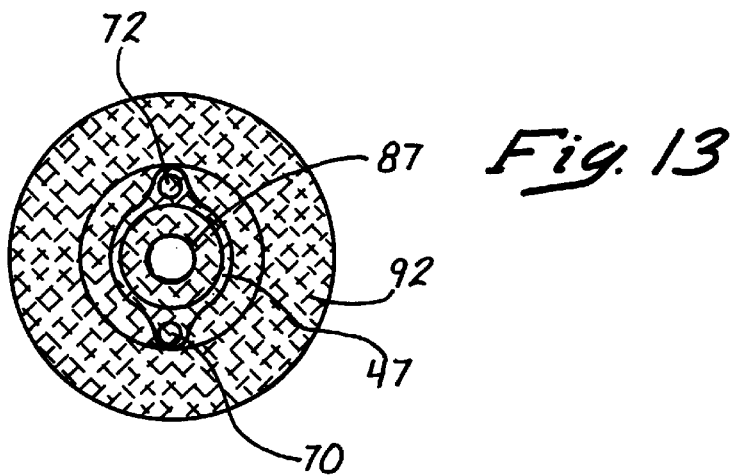
FIG. 13 is an end-view taken along lines 13—13 of FIG. 12 and showing the engagement mechanism in the path of the needles.
Figure 14:
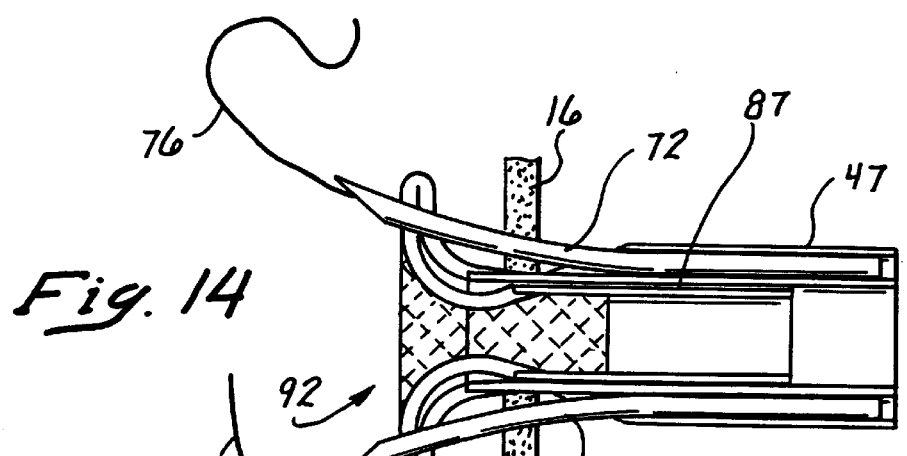
FIG. 14 is an axial cross-section view similar to FIG. 12 and illustrating the needles and sutures deployed through the engagement mechanism.

With the expandable structure 92 deployed in its high-profile state on the far side 30 of the wall 16, the needles 70, 72 can be deployed through the wall 16 on either side of the incision 12 and forced through the expandable structure 92. In FIG. 12, the respective paths of the needles 70, 72 are designated by the reference numerals 101 and 103. From this presentation, it can be seen that the expandable structure 92 in its high-profile state extends radially beyond the needle paths 101 and 103. With the needles 70, 72 extending through the expanded structure 92, as illustrated in FIG. 14, the sutures 32, 34 can be advanced by merely pushing distally on the proximal ends 74, 78. This advances the distal ends 76 and 81 of the sutures 32, 34 through the needles 72, 70, into the expanded structure 92 and perhaps to a position distal of the expanded structure 92.

Figure 15:
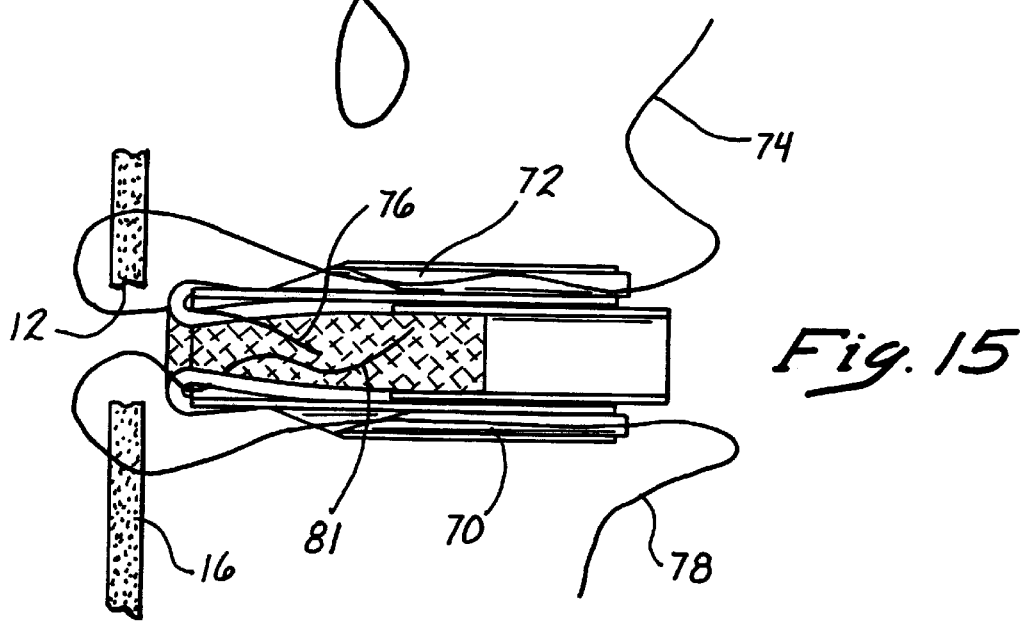
FIG. 15 is an axial cross-section view similar to FIG. 14 and illustrating the needles and engagement mechanism retracted with the suture ends captured in the mechanism.

At this point, the needle 70, 72 can be withdrawn by operation of the finger tab 61, 65. In a preferred method, the distal ends of the needles 70, 72, are drawn back through the expanded structure 92, back through the wall 16 and into the respective needle channels 50, 52, as illustrated in FIG. 15.

With the suture ends 81, 96 extending on the far side 30 of the wall 16, the expandable structure 92 can be operated to capture these suture ends prior to withdrawal of the apparatus 10 from the incision 12 and percutaneous cut 23. As illustrated in FIG. 15, this capture of the suture ends 76 and 81 can be facilitated by returning the expandable structure 92 to the low-profile state, and drawing the structure 92 proximally into the sheath 47.

As the suture apparatus 10 is withdrawn from the wall 16, the suture ends 76, 81 captured in the expandable structure 92 are moved from the far side 30 of the wall 16 back through the incision 12 to the near side 27 of the wall 16. As the entire apparatus 10 is further removed from the percutaneous cut 23, all four of the suture ends 74, 76, 78, and 81 are accessible exteriorly of the patient 14 as illustrated in FIG. 10.

As the suture ends 76, 81 are placed into the expanded structure 92, it is important that these ends 76, 81 be sufficiently embedded in or captured by the structure 92, for them to be removed from the surgical site. There is a slight resistance to this movement because the sutures pass through the tissue wall 16. As the suture ends 76 and 81 are drawn proximally, the suture ends 74 and 78 are moved distally through the needles 70, 72 and the wall 16.

Figure 17:
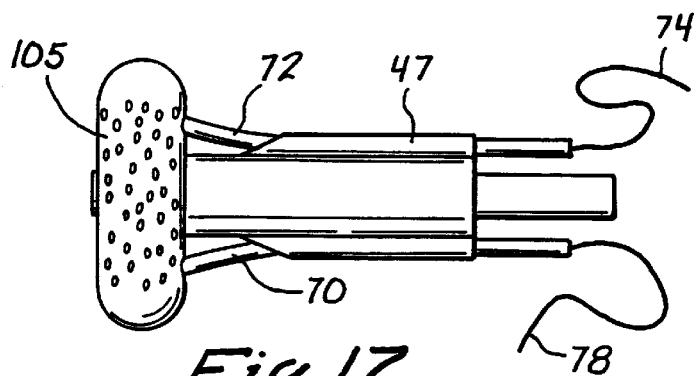
FIG. 17 and FIG. 17a are side elevation view similar to FIG. 16 illustrating the foam engagement mechanism in its deployed state.
Figure 17A:
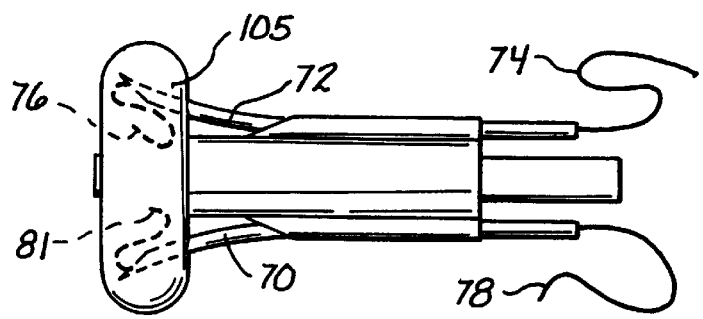

In order to facilitate the placement and capturing of the sutures 32, 34 in the expandable structure 92, the engagement mechanism 85 can be constructed of various materials and operated in various ways. A material of particular interest for the expandable structure might include foam, designated by the reference numeral 105. This foam 105 can be maintained in a low-profiled state as illustrated in FIG. 6, but is preferably expandable to a high-profile state as illustrated in FIG. 17. An expanded structure 92 made of the foam 105 can be provided as a solid material compressible to its low-profile state, but normally expandable to its high-profile state. The foam 105 can also be provided as a balloon-type structure having walls which are movable in the manner previously described. The compressibility of the foam 105 aids in capturing the suture ends 76 and 81 prior to removal of the apparatus 10 from the surgical site.

Figure 19:
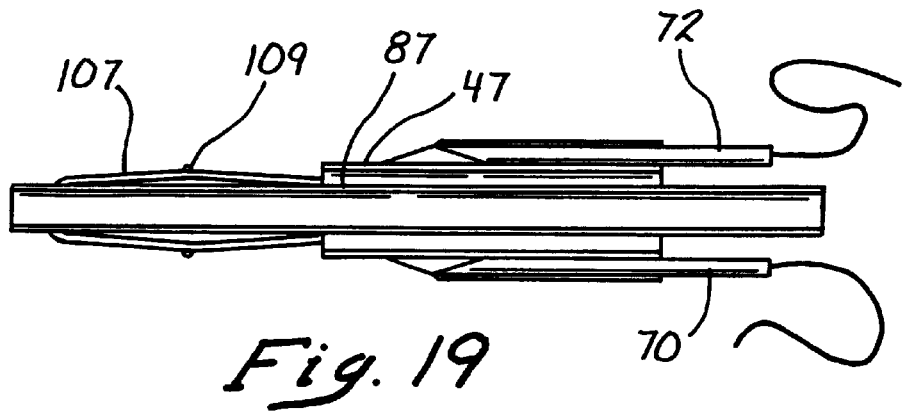
FIG. 19 is an axial cross-section view of a further embodiment wherein the suture engagement mechanism is formed of a solid material such as rubber.
Figure 20:
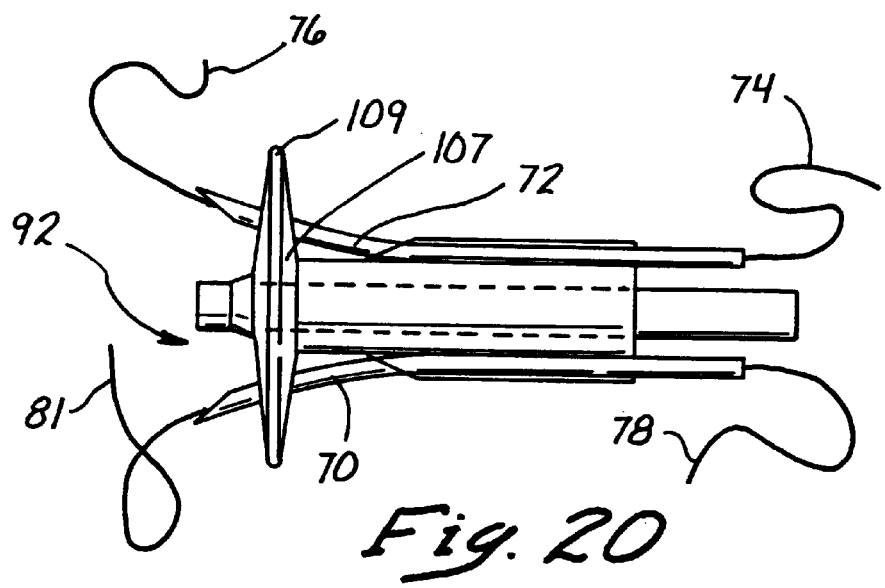
FIG. 20 is a side elevation view illustrating the rubber mechanism deployed with the needles and suture ends extending through the mechanism.

Another material of particular interest for the expandable structure 92 might include an elastic material such as latex or rubber, designated by the reference numeral 107 in FIG. 19. Forming the rubber 107 with a circumferential bead 109 facilitates deployment of the expandable structure 92 into its expanded state as illustrated in FIG. 20. In this case, the circumferential bead 109 facilitates a double-cone configuration for the rubber structure 94'.

Figure 16:
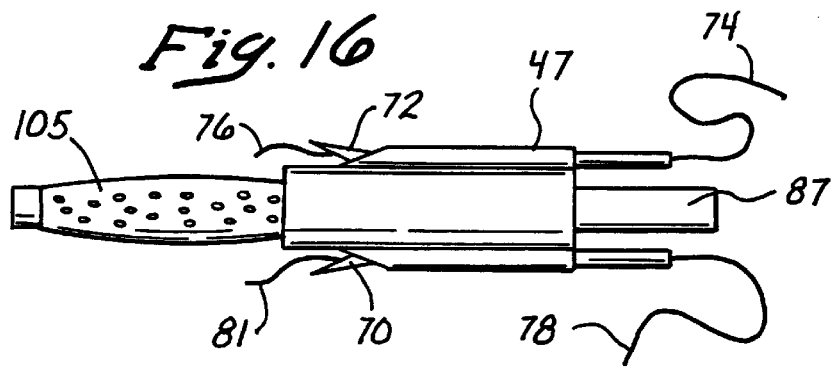
FIG. 16 is a side elevation view of a further embodiment wherein the engagement mechanism comprises foam and is illustrated in its advanced low-profile state.
Figure 18:
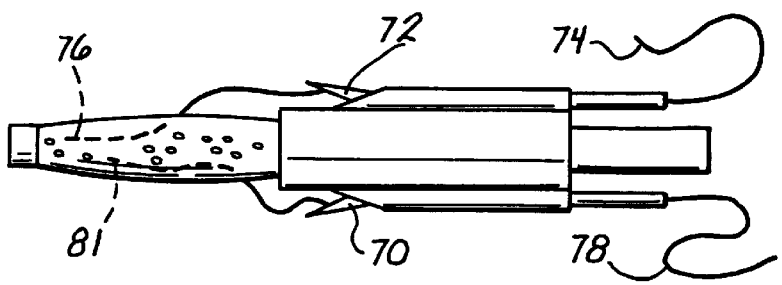
FIG. 18 is a side elevation view showing the foam engagement mechanism deployed and the needles and sutures ends advanced for capture by the mechanism.
Figure 21:
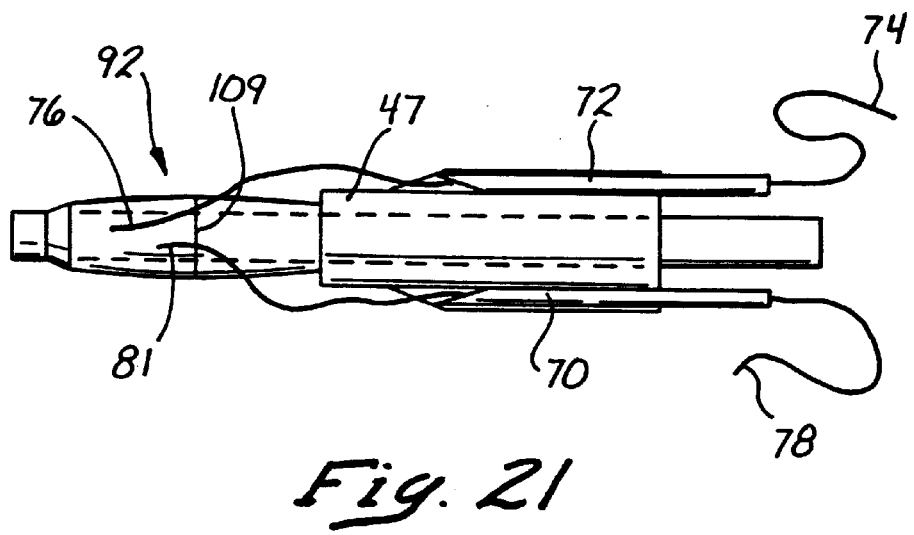
FIG. 21 is a side elevation view similar to FIG. 20 with the needles retracted and the suture ends captured in the expanded suture engagement mechanism.

As in the foam embodiment discussed with reference to FIGS. 16–18, the rubber structure 94 may be compressible to its low-profile state and automatically expandable to its high-profile state. The rubber structure 94 appears to be of particular advantage when the needles 70, 72 are advanced to penetrate the structure 92. Particularly in its expanded state, the rubber 107 will offer little resistance to this penetration by the needles 70, 72. Of even further advantage is the proportion of the rubber structure 94 which facilitates capture of the suture ends 76, 81. As the rubber 107 returns to its low-profile state, it tends to grip the suture ends 76, 81, firmly capturing them in the engagement mechanism 85. Thus, returning the rubber structure 94 to the low-profile state, as illustrated in FIG. 21, firmly captures the suture ends 76, 81 in the expandable structure 92.

Still a further embodiment of the expandable structure 92 might include a balloon structure 110 as illustrated in FIGS. 22–25. The balloon structure 110 has a low-profile state as illustrated in FIG. 22, but is inflatable to provide the high-profile state as illustrated in FIG. 23. This embodiment is of particular interest since the penetration of the inflated-balloon structure 110 by the needles 70, 72 punctures the balloon collapsing the balloon material around the needles 72, 74 and associated suture ends 76 and 81. Thus, the collapsing balloon structure 110 facilitates capture of the suture ends 76, 81, automatically. When the needles 70, 72 are withdrawn from the collapsed balloon structure 110, the inherent elastomeric characteristics of the balloon material firmly grip the suture ends 76 and 81. Withdrawing the balloon structure 110 into the sheath 47 may further compress the structure 110 and enhance the capture of the suture ends 76, 81 as illustrated in FIG. 25.

From the foregoing description of various embodiments of the expandable structure 92, it should be clear that in most embodiments its purpose is to not only receive the suture ends 76 and 81, but also capture these suture ends for ultimate withdrawal through the incision 12. As noted, this function can be facilitated with different variations and embodiments of the expandable structure 92. It should also be apparent that the capture function can be facilitated by various embodiments of the sutures 32, 34. For example, the suture ends 76 and 81 can be provided with structures which are easily insertable into the expandable structure 92, but inhibit removal from the structure 92. By way of example, the suture ends could be provided with a terminating device having a fish hook or barb configuration. Alternatively, the suture ends 76 and 81 could be provided with T-anchors, as disclosed and claimed by applicant in U.S. Pat. No. 5,626,614, issued on May 6, 1997, and entitled T-Anchor Suturing Device and Method for Using Same, which is incorporated herein by reference.

Figure 28:
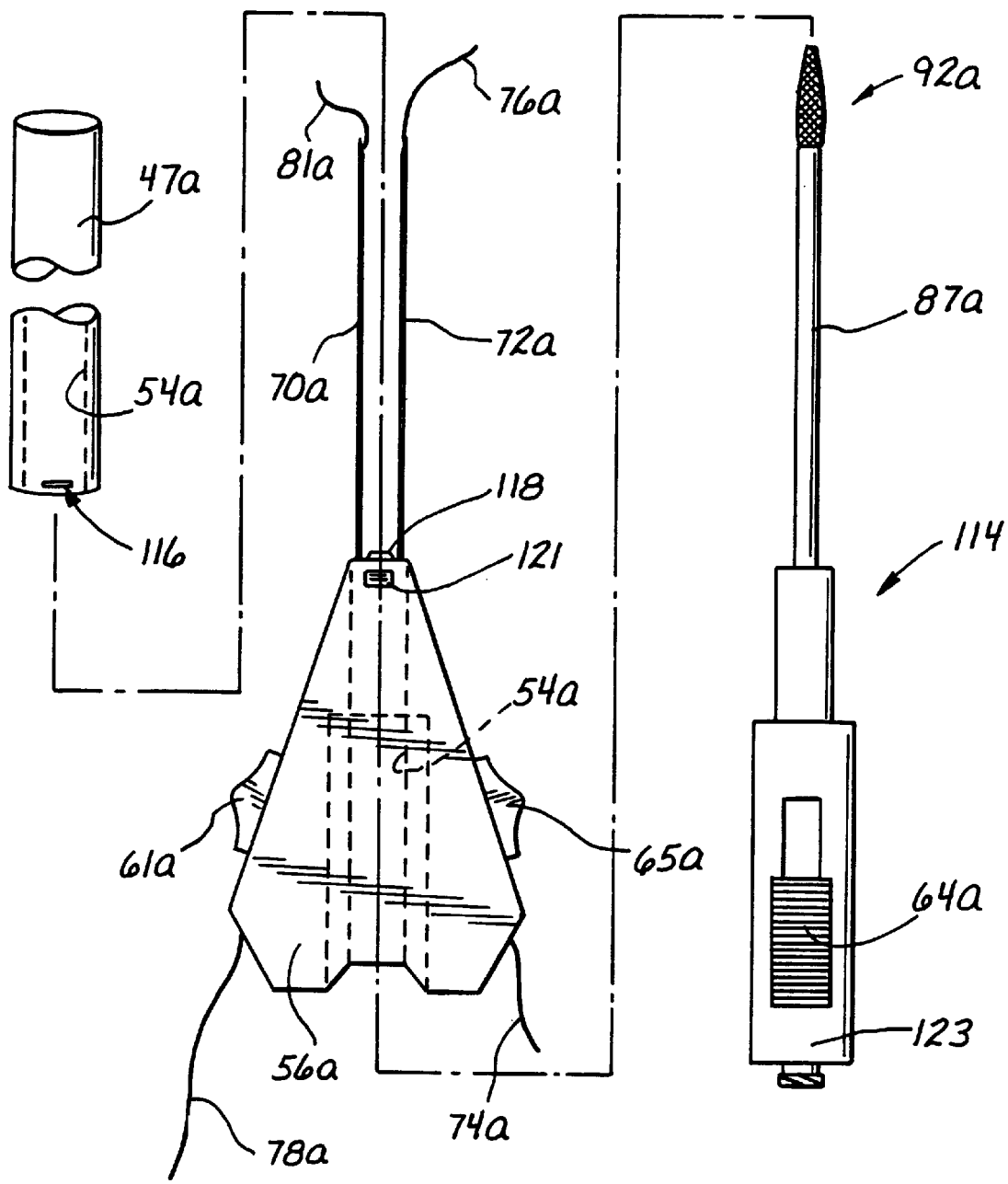
FIG. 28 is an exploded view of the embodiment illustrated in FIG. 26 having a removable suture engagement mechanism and a removable needle assembly.

A further construction for the sheath 47 can provide significant advantages in an alternative procedure associated with the suture apparatus 10. As illustrated in FIG. 26, this embodiment of the sheath 47 can be provided with needle channels 50, 52 which open along their entire length into the working channel 54. A cross-section of this embodiment is illustrated in FIG. 27 which is positioned next to FIG. 3 for comparison. This configuration of the sheath 47 facilitates an embodiment of the suture assembly 10 which includes a removable needle assembly 112 and removable suture engagement mechanism 114, as illustrated in FIG. 28. In this embodiment, elements of structure which are similar to those previously discussed will be designated by the same reference numeral followed by the lower-case letter "a".

As illustrated in FIG. 28, the proximal end of the sheath 47a can be provided with a tab slot 116, facilitating coupling to the needle assembly 112. In this embodiment, the needle assembly 112 includes the needles 70a, 72a, the handle assembly 56a, and the associated finger tabs 61a and 65a. The needle assembly 112 removably engages the slot 116 in the sheath 47a with a tab 118 operable by a tab release 121. The working channel 54a of the sheath 47a communicates with and extends entirely through the proximal end of the handle assembly 56a.

The suture engagement assembly 114, also illustrated in FIG. 28, is removably insertable into this working channel 54a. The suture engagement assembly 114 includes the extendable structure 92a, the elongate tube 87a, and a handle structure 123 which includes the finger tab 64a.

Operation of this embodiment of the suture assembly 10 is somewhat different from that previously described. With the apparatus 10 fully assembled, the needle structure 110 is attached to the tube 147a and the suture retention assembly 114 is inserted into the working channel 54a. The apparatus 10 is then inserted through the cut 23 and incision 12, the expandable mechanism 92a is deployed to its high-profile state, and the needles 70a, 72a are advanced. In the manner previously discussed, the sutures 32a, 34a are then moved distally and the distal ends 76a, 81a captured in the expandable structure 92a.

At this point in the procedure the suture-engagement assembly 114 can be removed from the working channel 54a drawing with it the distal ends 86a, 81a of the sutures 32, 34. The suture ends 76a, 81a emanate from the working channel 54a at the proximal end of the needle assembly 112, while the suture ends 74, 78 emanate from the needles 70a, 72a at the proximal end of the handle assembly 56a.

The needle assembly 112 can now be removed from the sheath 47a by operation of the tab release 121. In this step of the process, the proximal suture ends 74a, 78a are removed from the needles 70a, 72a. Importantly, with the needle channels 50a, 52a, extending into the working channel 54a, all of the suture ends 74a–81a now extend from the working channel 54a of the sheath 47a which has been left in place. With all four of the suture ends 74a–81a extending through the same working channel 54a, knots can be tied and pushed through the sheath 47a in its operative position. Thus, the sheath 47a provides access through the percutaneous cut 23 in the skin 25 all of the way up to the wall 16. This greatly facilitates tying of suture knots without the interference of surrounding tissue.

Variation on this embodiment of the invention might include the needle assembly 112 and suture engagement assembly 114 formed as a single unit which is disengageable and removable from the sheath 47a.

Figure 29:
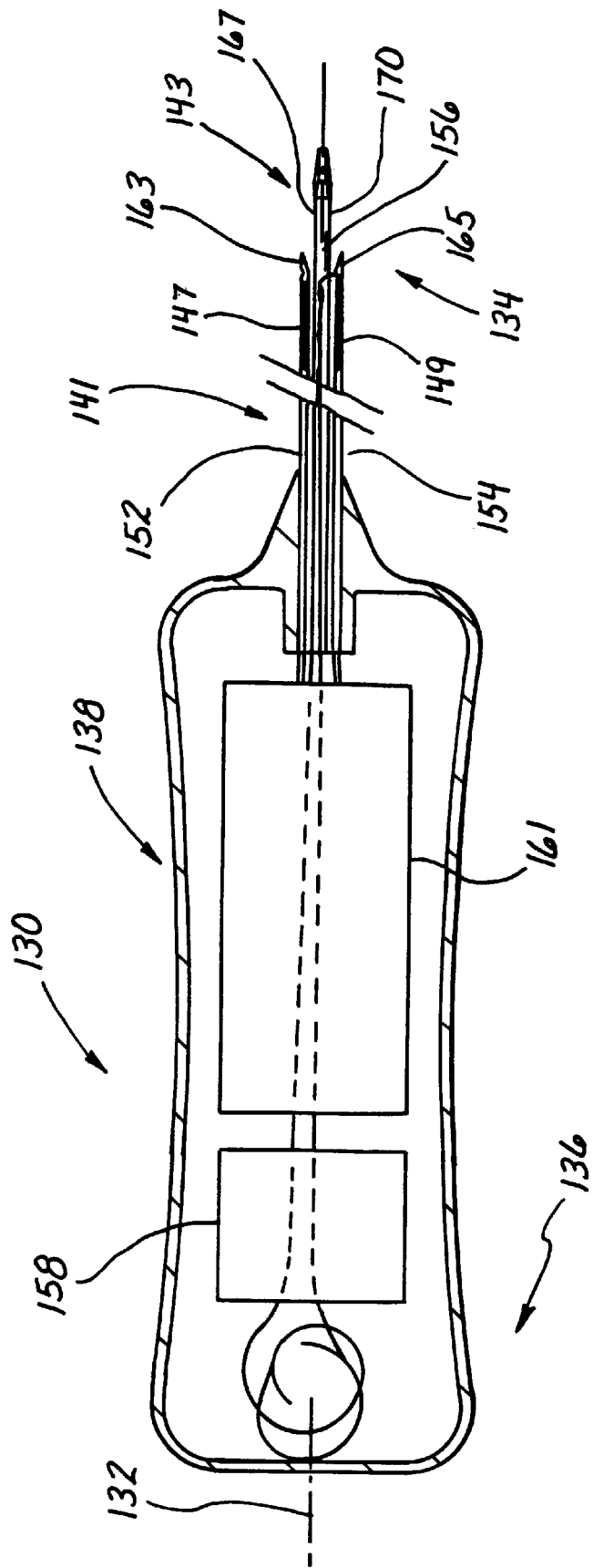

In a further embodiment of the invention illustrated in FIG. 29, an elongate suturing device 130 has an axis 132 which extends between a distal end 134 and a proximal end 136. A handle or housing 138 is disposed at the proximal end 136, and a shaft 41 with a hollow distal tip 143 is disposed at the distal end 134.

A suture 145 extends from the housing 138 and through the shaft 141 where it is manipulated by a first stylet 147 and a second stylet 149, each carried in a respective channel 152 and 154 of the shaft 141. These channels 152 and 154 in a preferred embodiment are positioned along opposite sides of a working channel 156 which extends axially through the shaft 141.

At the proximal end 136 of the device 130, a suture-tensioning mechanism 158 and a stylet-operating assembly 161 can be disposed within the handle or housing 138. In the manner described in greater detail, below, the stylet-operating assembly 161 enables a user at the proximal end 136 to operate the stylets 147, 149 at the distal end 134. This operation is facilitated by the suture-tensioning mechanism 158 in the manner described in greater detail below.

With an initial focus at the distal end 134 of the device 130, one can see in the side-elevation view of FIG. 30 that the stylets 147, 149 terminate in distal tips 163, 165, respectively, which can be flattened and sharpened. FIG. 29 also illustrates a pair of guide slots 167 and 170 associated with the stylets 147 and 149, respectively. These guide slots 167, 170 are formed on opposing sides of the shaft 141 and provide access into the working channel 156 of the hollow distal tip 143.

In FIG. 30, the device 130 is illustrated to be operatively disposed with the proximal shaft portion 142 extending up to the tissue wall 16 on the near side 27, and the remainder of the shaft 141 including the hollow distal tip portion 143 extending through the wound 12 to the far side 30 of the wall 16. This enlarged side view is particularly beneficial in illustrating the configuration of the guide slots 167, 170 in a preferred embodiment. As noted, these slots 167, 170 extend along opposing sides of the shaft 141 and provide access into the hollow interior region of the distal tip 143. The slots 167, 170 are defined in part by distal portions 171, respectively, in this embodiment.

Also illustrated in FIG. 30 are a pair of openings associated with the distal tips 143, 145 of the stylets 147, 149. In the distal tip 165, the opening is formed centrally of the tip 165 in the shape of a hole 172. In the distal tip 163, the opening is formed along the outer side of the tip 163 and has the shape of a hook 174. In the manner discussed in greater detail, below, the suture 145 is initially threaded through the hole 172 of the stylet 149 and ultimately engaged by the hook 174 of the stylet 147.

This entire procedure is illustrated in the progressive views of FIG. 31 through FIG. 38. As was the case with FIG. 30, these views illustrate only the distal end 134 with the proximal shaft portion 142 disposed on the near side 27 of the wall 16, and the remainder of the shaft 141 extending through the wound 12 to the distal side 30 of the wall 16.

When the suturing device 130 is initially disposed in this operative position, the stylets 147 and 149 will typically be retracted into their respective channels 152, 154 in the proximal shaft portion 142. Alternatively, the stylets 147, 149 can be positioned slightly distally of the proximal shaft portion 142 so that the initial placement of the device 130 in its operative position forces the stylets 147, 149 through the wall 16 creating respective tissue holes 181 and 183 in close proximity to, but on opposing sides of, the wound 12. This alternative structure and method is illustrated in FIG. 31.

It will also be noted in FIG. 31 that the suture 145 is preferably threaded to extend through the working channel 156 of the shaft 141, through the slot 170 in the shaft 141, and through the hole 172 in the distal tip 165 of the stylet 149.

Figure 32:
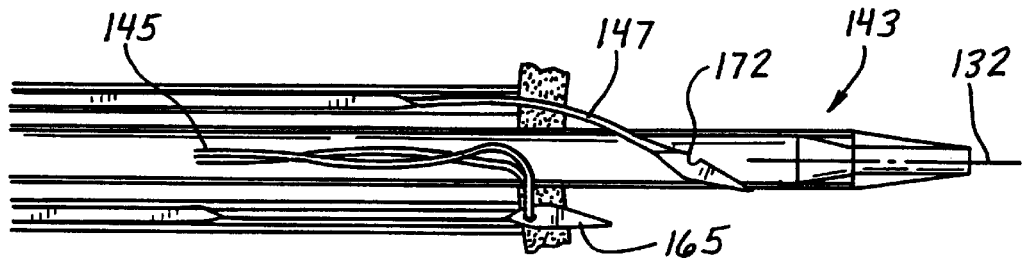

In accordance with a preferred method of operation, the first stylet 147 is initially advanced to an extended position as illustrated in FIG. 32. As the stylet 147 is advanced within its channel 152, it also advances through the tissue hole 176 as it curves through the guide slot 167 to its distal-most position illustrated in FIG. 32. It will be noted that, in this position, the distal tip 163 has preferably passed entirely through the guide slot 167 and partially through the guide slot 170. The hook 172 in the distal tip 163 is positioned within the distal tip 143 of the shaft 141.

It is of particular interest to note that the stylet 147 can be formed of a material such as Nitinol to provide it with memory characteristics so that the arc, curve, or bend in the stylet 147 occurs automatically. With these characteristics, the stylet 147 automatically moves from a generally straight configuration within the channel 152 to a curved configuration so that its path passes through the wall 16 and curves on the far side 30, through the slot 167, and across the axis 132.

Figure 33:
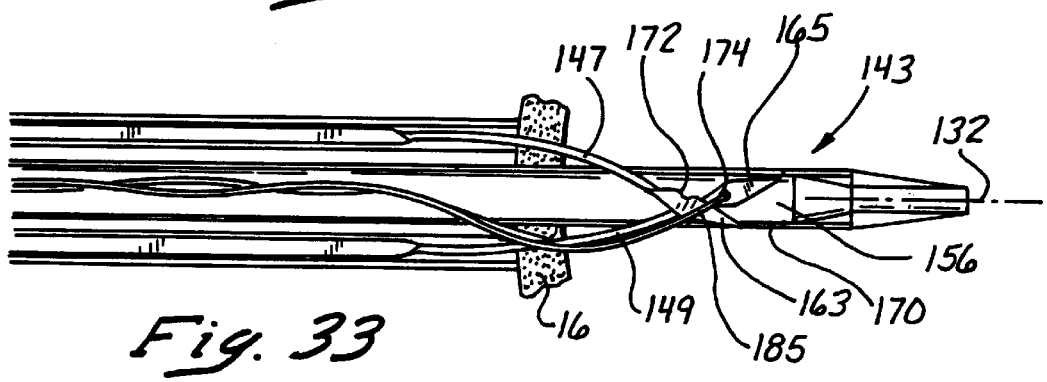

With the stylet 147 operatively positioned as illustrated in FIG. 32, the second stylet 149 can now be advanced to its distal-most position as illustrated in FIG. 33. In a manner similar to that associated with the stylet 147, the stylet 149 is advanced through its associated tissue hole 178 and through the guide slot 170 into the working channel 156. Preferably, the stylet tip 165 extends across the axis 132 so that the stylet 147 and the stylet 149 intersect within the hollow distal tip 143 of the shaft 141.

With the suture 145 threaded through the hole 172, this movement of the stylet 149 brings the suture into the working channel 156. Importantly, during this step illustrated in FIG. 33, the stylet tip 165 passes in close proximity and preferably in contact with the stylet tip 163, as perhaps best illustrated in FIG. 30. The path of the stylet 149 is also such that the hole 172 passes around the end of the stylet tip 163 so that the suture 145 carried by the tip 165 is passed over the tip 163.

Figure 34:
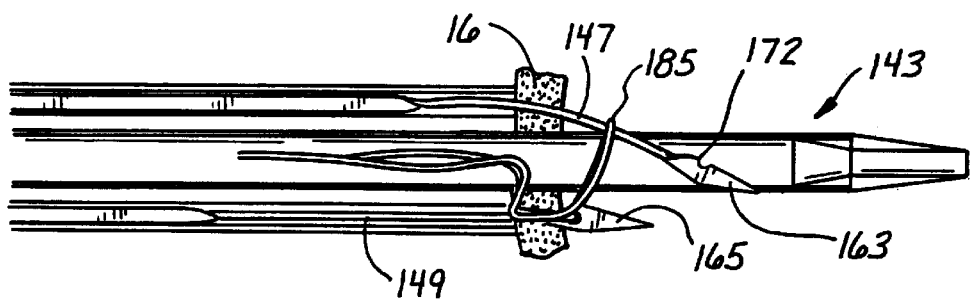

The importance of this passage of the stylet tip 165 relative to the stylet tip 163 is best illustrated in FIG. 34 which shows the stylet 149 retracted from the slot 170 into a space relationship with the shaft distal tip 143. If the suture 145 is passed over the stylet tip 163, as illustrated in FIG. 33, then a suture loop, designated by the reference numeral 185, will remain over the stylet 147 as the stylet 149 is withdrawn.

Figure 35:
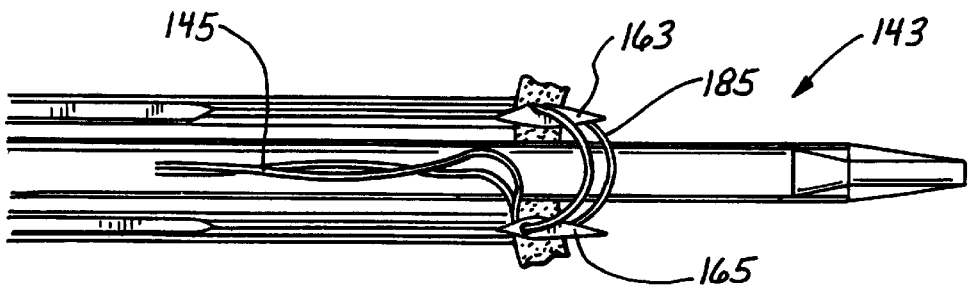
Figure 36:
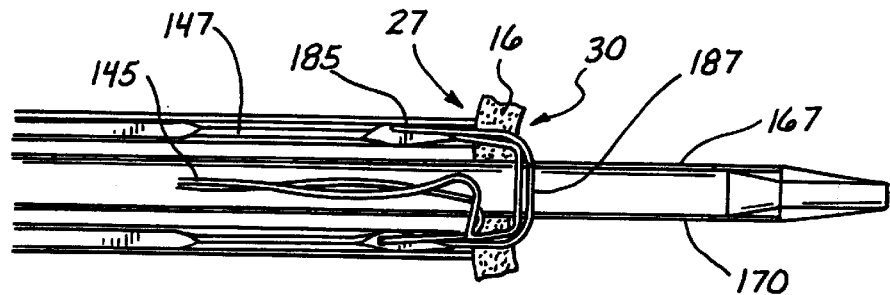

The next step in a preferred method is to engage the suture loop 185 with the hook 172, and to withdraw the stylet 147 as illustrated in FIG. 35.

Further proximal movement of the stylets 147 and 149 moves the suture loop 185 to the near side 27 of the wall 16. It will noted with reference to FIG. 36 that the free ends of the suture 145 are already on the near side 127, but now an intermediate suture portion, designated by the reference numeral 187, extends through the guide slots 167, 170 of the shaft 141 on the far side 30 of the wall 16.

Figure 37:
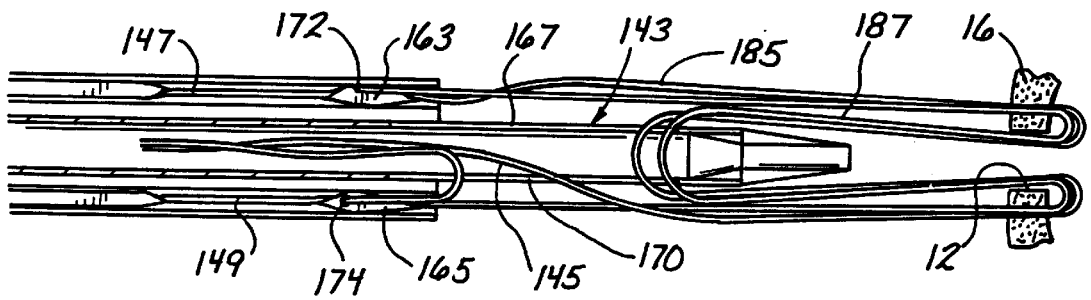

FIG. 37 illustrates the next step in a preferred method wherein the suturing device 130 is withdrawn through the wound 12. In this view, it can seen that the intermediate suture portions 187 are engaged by the distal slot portions 171 as the device 130 is moved proximally. This engagement by the distal tip 143 of the shaft moves the intermediate suture portions 187 to the near side 27 of the tissue wall 16. As finally illustrated in FIG. 8, this removal of the device 130 from the wall 16 leaves multiple suture ends on the near side 27 of the wall 16 that can be tied in any configuration desired by the surgeon to close the wound 12.

Figure 38:
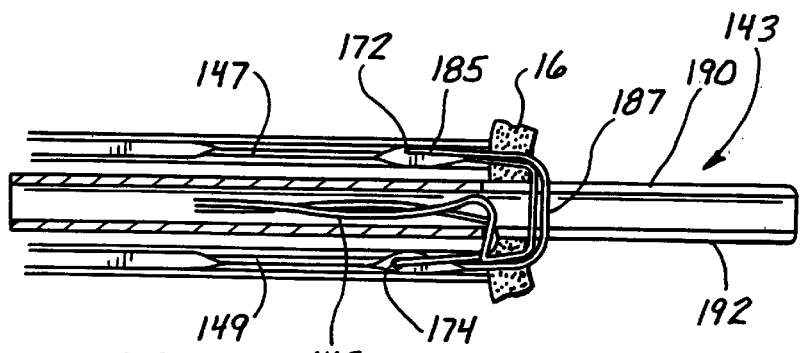
FIG. 38 and FIG. 39 illustrate a further embodiment of the device having guide slots opened at the distal end of the shaft.
Figure 39:
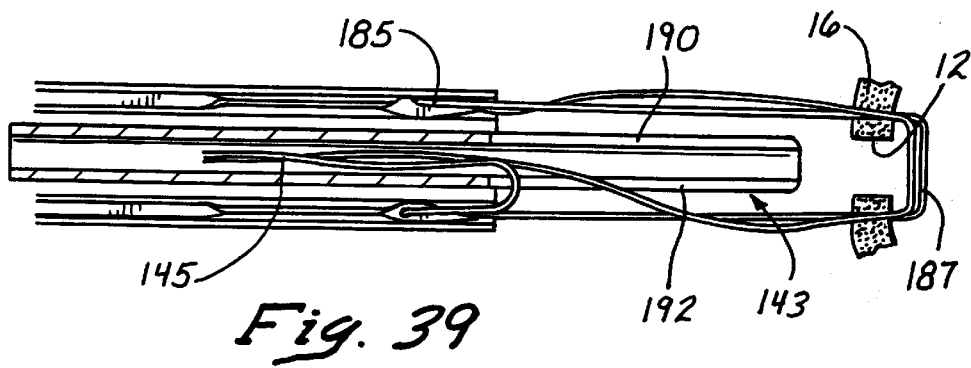

A further embodiment of the invention is illustrated in FIGS. 38 and 39. This embodiment is similar to that of FIG. 29 except for the guide slots 190 and 192. These slots 190, 192 are similar to the slots 167 and 170 in FIG. 29 in that they extend longitudinally on opposing sides of the shaft 141. However, the slots 190 and 192 extend to the end of the distal tip 143 of the shaft 141. There are no shaft portions, such as those designated by the reference numerals in FIG. 30, to close the distal end of the slots 190, 192.

The operative effect of this structure is best shown in FIG. 39 where the suturing device is illustrated in a view comparable to FIG. 38. In FIG. 39, however, it can be seen that with the guide slots 190 and 192 extending to the end of the distal tip 143, the intermediate suture portions 187 are free to exit the distal tip 143 as it moves through the wound 12. This leaves the free end of the suture 145 and the suture loop 185 extending on the near side 27 of the wall 16, while the intermediate suture portion 187 remains on the far side 30 of the wall 16. Once again, the suture ends on the near side 27 of the wall 16 can be tied in any desired configuration to close the wound 12.

Having discussed the operative distal end of the device 130 in several embodiments, it is now of interest to return to the proximal end 134 and operation of the suture tensioning mechanism 158 and stylet operating assembly 161 initially illustrated in FIG. 29.

Figure 40:
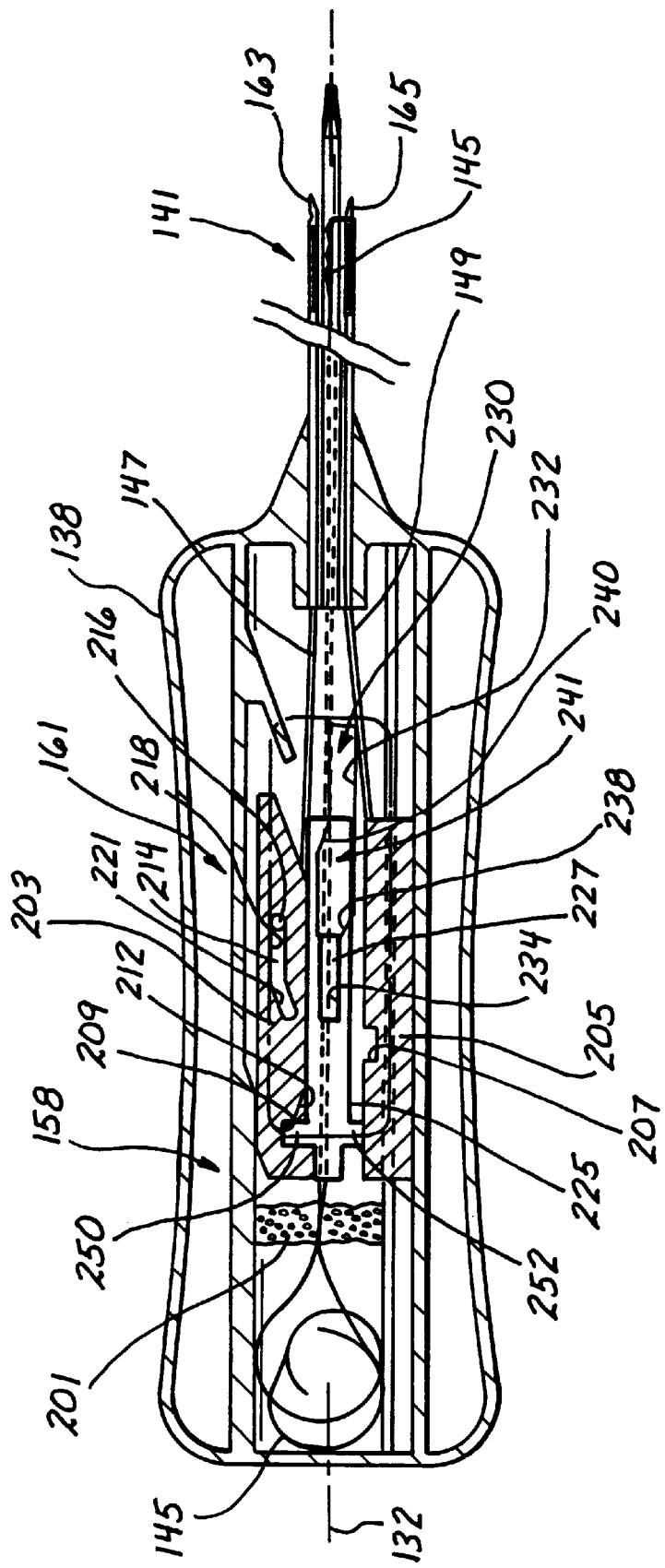
FIG. 40 is a top plan view illustrating an embodiment of a handle assembly and suture-operating mechanism which could be adapted for use with either the additional embodiment of FIG. 29 or the further embodiment of FIG. 39.

In FIG. 40, the suture-tensioning mechanism 158 is illustrated in the form of sponge 201 through which the suture 45 is passed as it extends into the shaft 141. The friction between the sponge 201 and the suture 145 maintains sufficient tension on the suture 145 to facilitate placement of the suture loop 185 around the stylet tip 163, as discussed with reference to FIG. 33. Certainly, the function of the suture-tensioning mechanism 158 can also be accomplished with other devices and materials providing a coefficient of friction sufficient to engage the suture 145. Alternatively, the mechanism 158 may include means defining a torturous path or other structure adapted to resist movement of the suture 145 in the distal direction.

A preferred embodiment of the stylet-operating assembly 161 is also illustrated in FIG. 40. In this case, the assembly 161 includes a pair of slides 203 and 205 attached, respectively, to the stylets 147 and 149. These slides 203 and 205 will typically have a planar configuration and will be adapted to move longitudinally within the housing 138 to control operation of the respective stylets 147 and 149.

The slide 205 attached to the stylet 149 has a notch 207 formed along its inner edge. In this particular embodiment, the slide 205 moves generally axially within the housing 138 without any substantial lateral movement.

By comparison, the slide 203 attached to the stylet 147 also includes a notch 209 which extends along the inner edge of the slide 203. On the distal side of the slot 209, the inner edge of the slide 203 is provided with a ramp 212 which extends distally inwardly toward the axis 132. A guide slot 214 is formed in the slide 203 and keyed to a pin 216 fixed to the housing 138. In distal portions 218, the slot 214 extends generally axially; however, in proximal portions 221, the slot 214 extends proximally inwardly toward the axis 132. With the slot 214 thus configured, the slide 203 is adapted to move axially as the slot portions 218 are keyed to the pin 216, and adapted to move both axially and laterally as the slot portions 221 are keyed to the pin 216.

Disposed between the slides 203 and 205 is a third slide 225 having a thumb tab 227 which extends through the housing 138 and is accessible to the user. The thumb tab 227 is movable within a slot 230 defined by the housing 138, the slot including a distal slot portion 232, a proximal slot portion 234. These slot portions 232 and 234 are displaced axially from each other by a pair of ramps 238 and 240 which define a transition zone 241 of the slot 230. The slide 225 associated with the finger tab 227 includes a projection 250 which extends toward the slide 203 and a projection 252 which extends toward the slide 205.

In the following discussion, reference will be made to FIGS. 41–46 in discussing the progressive operation of the stylet-operating assembly 161 at the proximal end 136 of the suturing device 130. These FIGS. 41–46 are keyed to FIGS. 31–36 previously referred to in a discussion relating to the stylets 147 and 149 at the distal end 134 of the suturing device 130.

Figure 41:
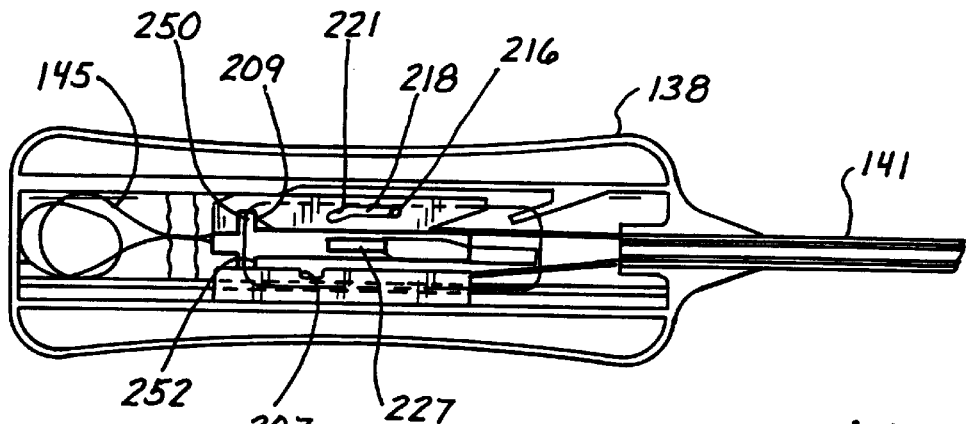
FIG. 41 through FIG. 46 illustrate progressive method steps in the operation of a stylet-operating assembly.
Figure 42:
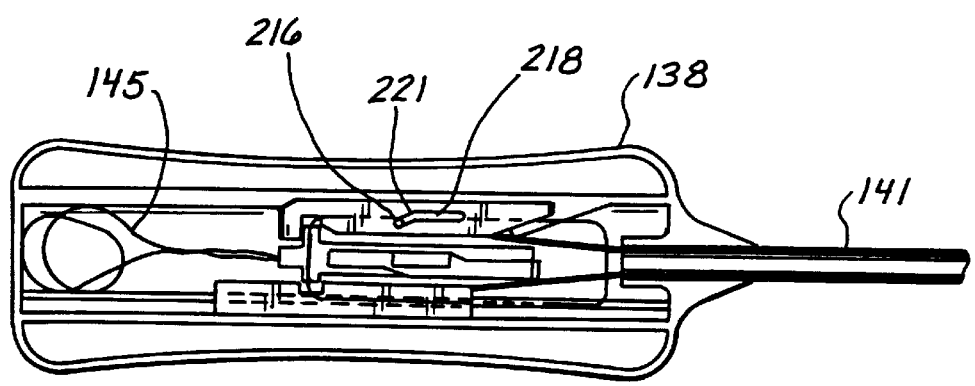
Figure 43:
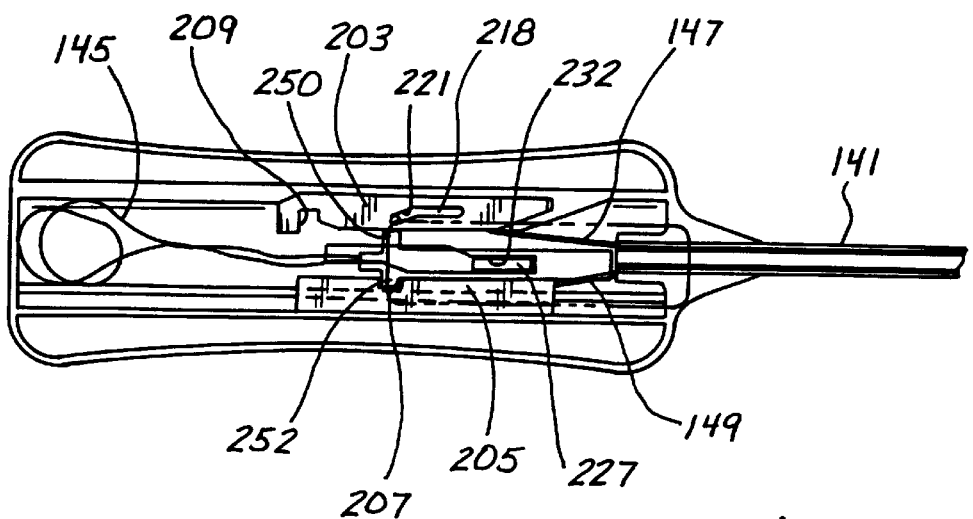
Figure 44:
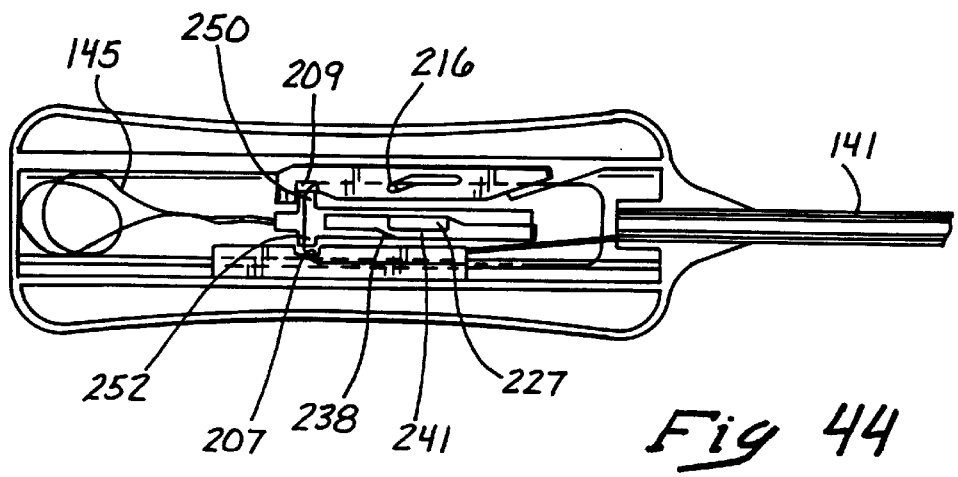
Figure 45:
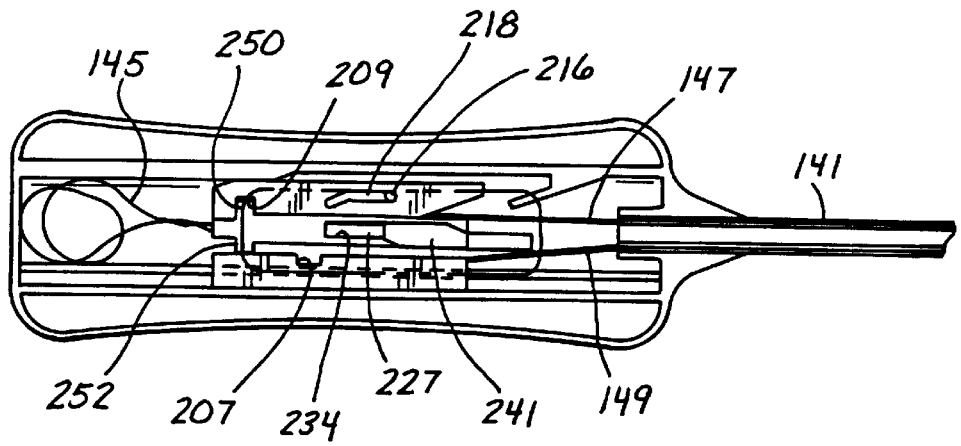
Figure 46:
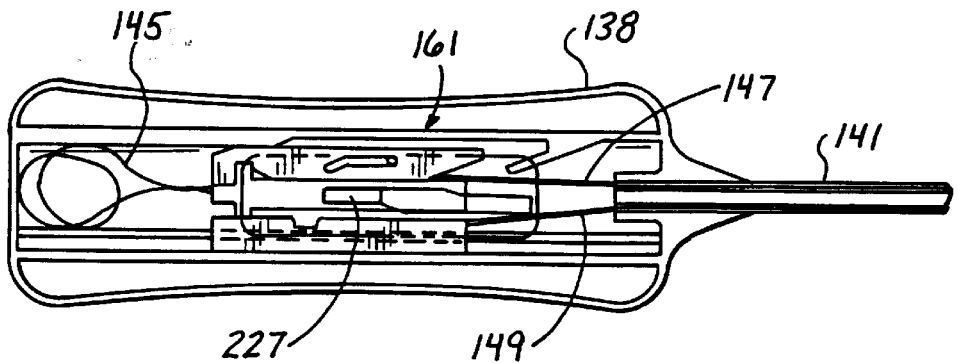

In operation, the suturing device 130 is initially positioned as illustrated in FIG. 41 with the thumb tab 227 seated in the slot portion 234, the projection 250 seated in the notch 209, and the pin 216 located at the distal end of the slot portion 218. From this initial position, the operator holding the handle 138 can move the thumb tab 227 distally until the pin 16 is seated in the proximal end of the slot portion 221, as illustrated in FIG. 42. This will bring the thumb tab 227 into the transition zone 241 and up to the ramp 240. Lateral movement of the slide 203, occasioned by the angled configuration of the slot 214, will remove the notch 209 from the projection 250 which is then proximate to the ramp 212 on the edge of the slide 203. This forward movement of the slide 203 is accompanied by forward movement of the stylet 147 as illustrated in FIG. 32.

Further movement of the thumb tab 227 in the distal direction causes the thumb tab 227 to ride along the ramp 240 thus moving the slide 225 longitudinally and laterally of the slide 203. With this position illustrated in FIG. 43, the tab 250 of the slide 225 rides along the ramp 212 of the slide 203 which remains in the location illustrated in FIG. 42.

The lateral movement of the thumb tab 227 and associated slide 225 causes the projection 252 to engage the slot 207 in the slide 205. This happens immediately as the thumb tab 227 moves along the ramp 240 so that further movement of the thumb tab 227 into the slot portion 232 also moves the slide 205 distally. Of course, this distal movement of the slide 205 is accompanied by distal movement of the stylet 149 to its distal-most position illustrated in FIG. 33. This important step is also characterized by the suture loop 185 being placed over the stylet tip 163 as previously discussed.

Once this step has been accomplished, the user can return the thumb tab 227 to the transition zone 241. As part of this process, the tab 227 will ride up on the ramp 238 and thereby move the slide 225 axially and distally, withdrawing the stylet 149 to the position illustrated in FIG. 34. Near the end of this distal movement, the thumb tab 227 will ride on the ramp 238 moving the associated slide 225 laterally so that the projection 252 disengages the notch 207. This disengagement of the notch 207 is accompanied by engagement of the notch 209 by the projection 250. Thus, this position of the slides 203 and 205 is commensurate with the position of the stylets 247 and 249 illustrated in FIG. 34.

Further movement of the thumb tab in the distal direction moves the slide 203 proximally until the pin 216 reaches the distal end of the slot 218. This proximal movement of the slide 203 is accompanied by proximal movement of the stylet 147 to the position best illustrated in FIG. 35. In this final position, the thumb tab 227 is seated in the proximal portions 234 of the slot 241.

In a final phase of operation, the suturing device 130 can be totally removed from the wound 12 as illustrated in FIG. 38. Although the thumb tab 227 remains in its final position during this step, the entire device 130 is moved proximally away from the wall 16 leaving the suture configuration illustrated in FIGS. 38 and 40 for the alternative embodiments of those figures.

In several of these embodiments, the stylets 147 and 149 automatically curve on the far side 30 of the wall 16 to intersect within the distal end of the shaft 141. In these embodiments, transfer of the suture loop 185 occurs directly. For example, the suture loop 185 carried by the stylet 149 is transferred directly to the stylet 143 as illustrated in FIG. 33.

Figure 47:
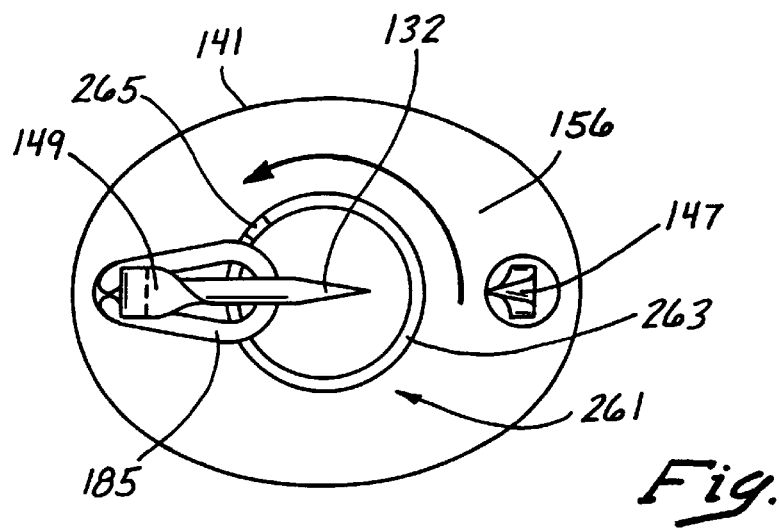
FIG. 47 is an end view of a further embodiment of the invention including a suture-transfer mechanism.

It is also within the concept of this invention to provide the stylets 147 and 149 with a straight configuration not only on the near side 27 but also on the far side 30 of the wall 16. In such an embodiment a suture-transfer mechanism, such as that designated by the reference numeral 261 in FIG. 47, can be provided to pick up the suture loop 185 from the stylet 149 and to carry that loop 185 to the stylet 147. In such an embodiment, the stylets 147 and 149 remained in a spaced relationship and the mechanism 261 merely carries the suture loop 185 between the spaced stylets 147, 149.

Figure 48:
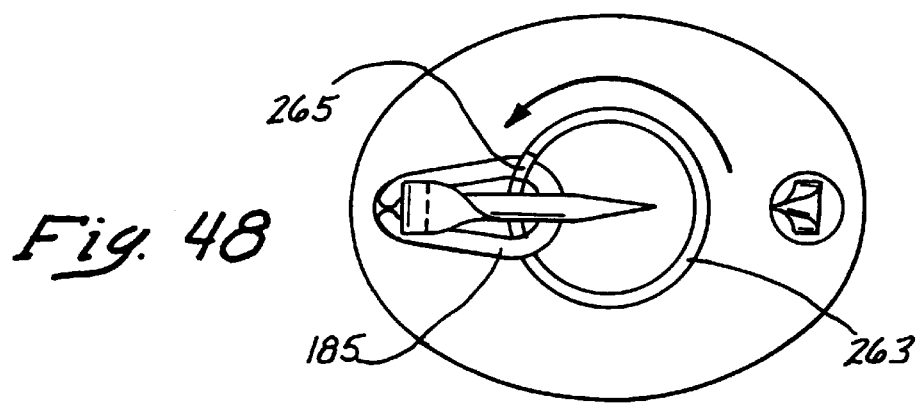
FIG. 48 is an end view similar to FIG. 47 and illustrating second stylet in an advanced position and operation of the suture-transfer mechanism to engage the suture loop on the second stylet.
Figure 49:
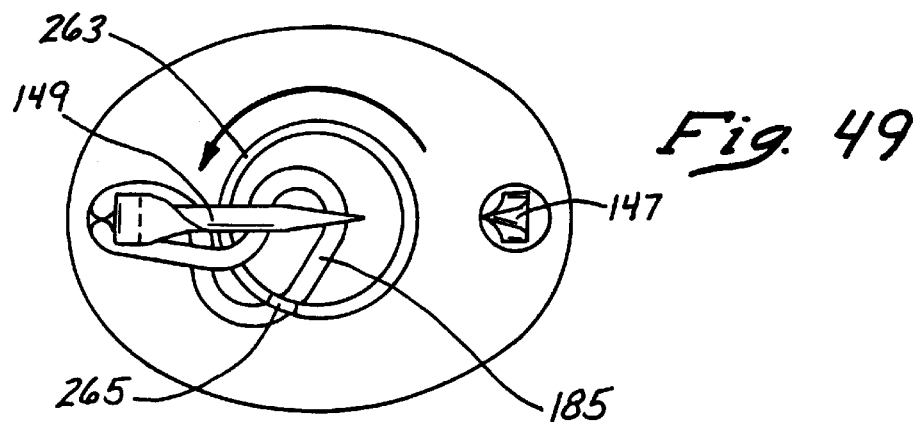
FIG. 49 is an end view similar to FIG. 48 and illustrating operation of the suture-transfer mechanism to move the suture loop from the second stylet toward the first stylet.
Figure 50:
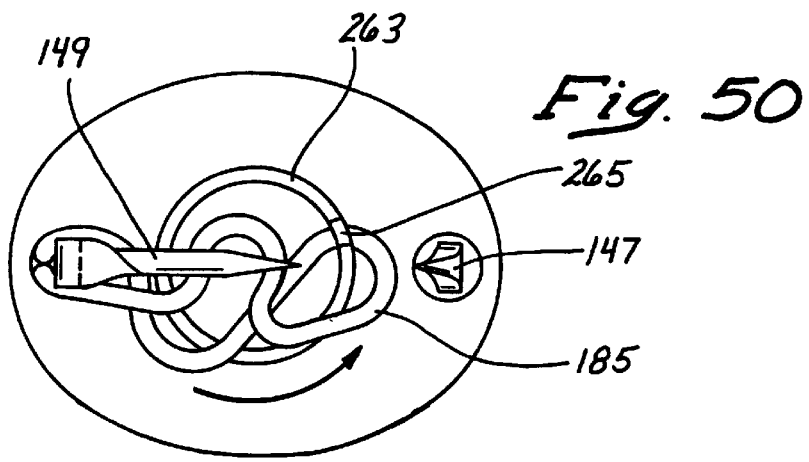
FIG. 50 is an end view similar to FIG. 49 and illustrating operation of the suture-transfer mechanism to position the suture loop next to the first stylet.
Figure 51:
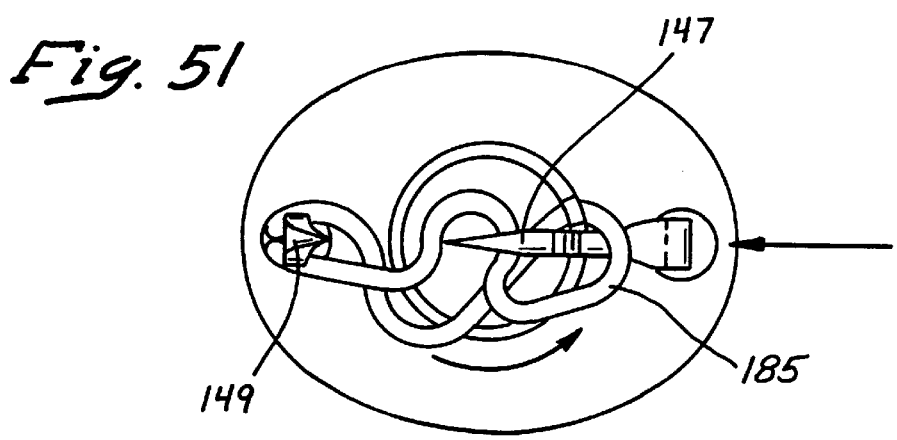
FIG. 51 is an end view similar to FIG. 50 and illustrating advancement of the second stylet to engage the suture loop.
Figure 52:
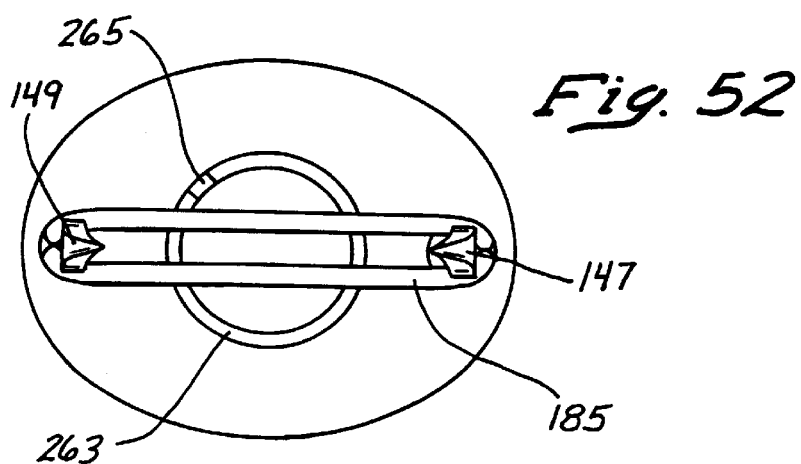
FIG. 52 is an end view similar to FIG. 51 and illustrating engagement of the suture loop by both the first stylet and the second stylet.

The suture-transfer mechanism 261, of course, can take many forms. One form contemplated includes a tubular stylet 263 extending entirely through the housing 138 (FIG. 29) and the working channel 156 of the shaft 141. This stylet, in a preferred embodiment, is movable longitudinally and rotatably along the axis 132 by operation of a proximal knob (not shown). The distal end of the stylet 263 is preferably formed with a notch 265 on its circumference. By rotating the stylet 263, the notch 265 can be brought into proximity with the stylet 149 where it engages the suture loop 185 as illustrated in FIG. 48. Then the stylet 263 can be rotated to move the notch 265 and the engaged suture loop 185 into proximity with the stylet 147, as illustrated in FIGS. 49 and 50. In accordance with a preferred method, the stylet 147 can then advance to engage the suture loop 185, as illustrated in FIG. 51, and retracted to spread the suture loop 185 between the stylets 147 and 149, as illustrated in FIG. 52. After transferring the suture loop 185 to the stylet 263, the suture-transfer mechanism 261 can be withdrawn into the shaft 141. The stylets 147 and 149 can then be moved proximally and the suturing device 10 withdrawn from the wound 12.

Variations on this concept might include an embodiment where the stylets 147 and 149 do not curve toward the axis 132, but rather remain in a generally parallel relationship. In such an embodiment, the suture-transfer mechanism 261 would engage the suture loop 185 and carry the loop over the opposing stylet 147. In such a structure, the suture-transfer mechanism 261 might take the form of a Nitinol wire axially deployable with a distal end laterally extending into proximity with the stylet 149 and rotatable to move the suture loop 185 into proximity with the stylet 147.

Although the concept of the arm formed from Nitinol wire is particularly advantageous, many other transfer mechanisms will be apparent to those skilled in the art. In general, any embodiment providing stylets 147 and 149 with a space relationship on the far side of the wall 16 can benefit from a transfer mechanism that will engage the suture 145 at one spaced location and move the suture 145 to another spaced location on the far side of the body wall.

Figure 52A:
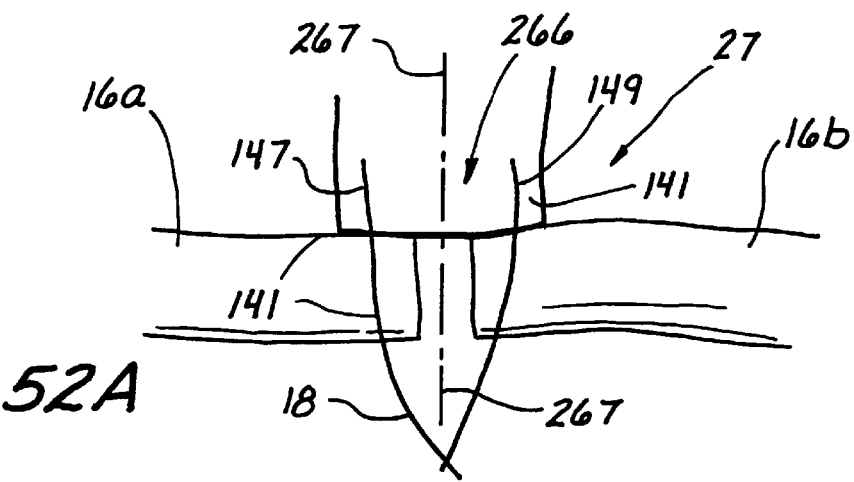
FIG. 52a is a side elevation view of two separate pieces of tissue having a relatively thin configuration and joined by the suturing apparatus of the present invention.

Most of the foregoing disclosure has been directed to closure of a wound or incision in a single piece of body tissue referred to as the body wall 16. It should be readily apparent that this device is equally advantageous for suturing first and second pieces of body tissue designated by the reference numerals 16a and 16b in FIG. 52a. These pieces 16a, 16b are separated by an area of intersection 266 which may be little more than a plane of separation 267. Ideally, if the tissue pieces 16a, 16b are relatively thin, the stylets 147 and 149 can pass through the respective pieces 16a, 16b and transfer the suture 145 on the far side 30 of the pieces 16a and 16b.

Figure 52B:
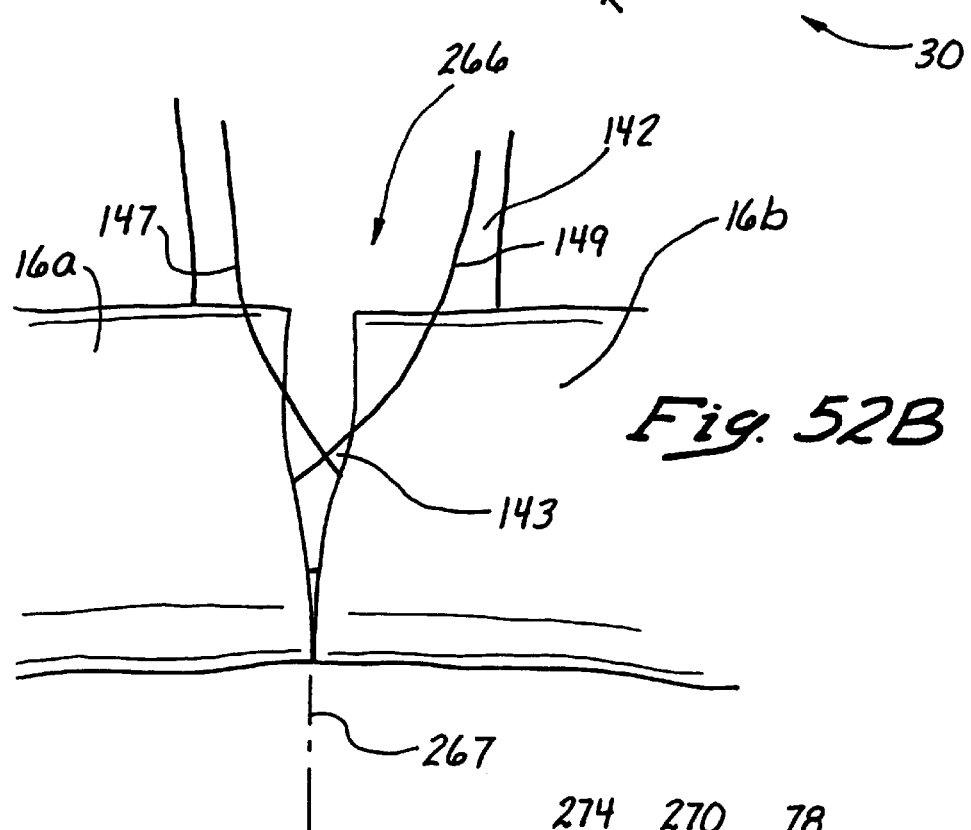
FIG. 52b is a side elevation view similar to FIG. 52a wherein the tissue pieces have a thicker configuration and a hollow distal tip of the device agent creating an area of separation.

Alternatively, the tissue pieces 16a and 16b may be relatively thick and disposed in adjacent contacting relationship as illustrated in FIG. 52b. In this case, the area of separation 266 may only be a plane of separation 267. In this embodiment, providing the shaft 141 with the hollow distal tip 143 can be of particular advantage. In this case, the hollow distal tip 143 can be inserted along the plane of separation 267 to widen the area of separation 266 and thereby provide additional space within which the suture transfer can take place.

Figure 53:
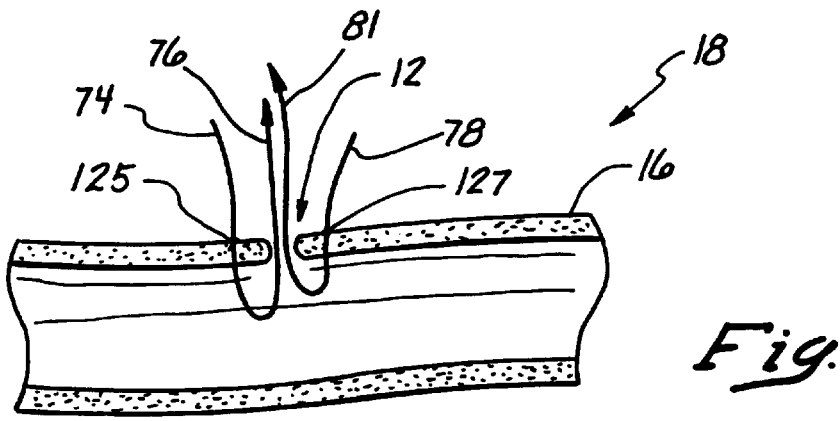
FIG. 53 is a side elevation view of the vessel illustrating four suture ends after removal of various embodiments of the device.

Having disclosed multiple embodiments of the suture apparatus 10, each offering particular advantages to the associated suturing process, it is apparent in several of these cases that the surgeon is left with four suture ends 74–81 extending from the vessel 18 as illustrated in FIG. 53. The distal suture ends 76, 81 extend through the incision 12 in the wall 16 while the proximal suture ends 74, 78 extend through the respective needle holes 125, 127 on either side of the incision 12.

Figure 56:
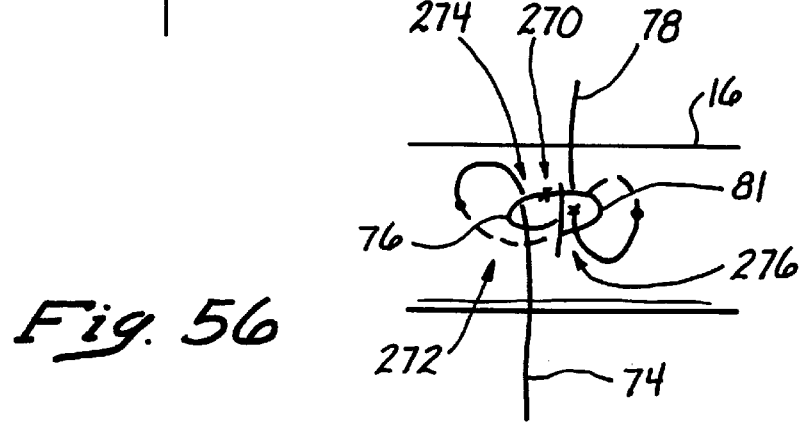
FIG. 56 is a top, plan view of the suture loop of FIG. 54 illustrating a first side and a second side of the loop and a method for threading of the loop from opposite sides with the free ends of the sutures.
Figure 54:
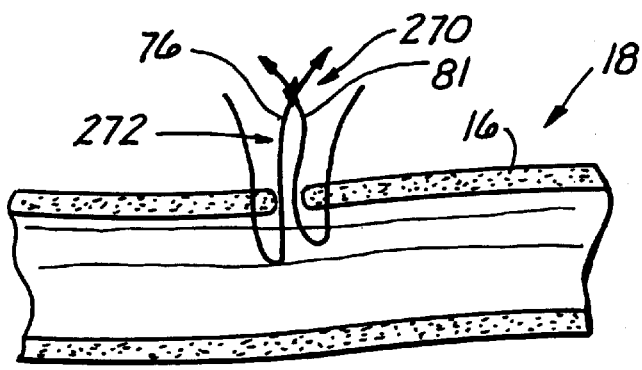
FIG. 54 is a side elevation view similar to FIG. 53 and illustrating the tying of a first knot to form a loop.
Figure 55:
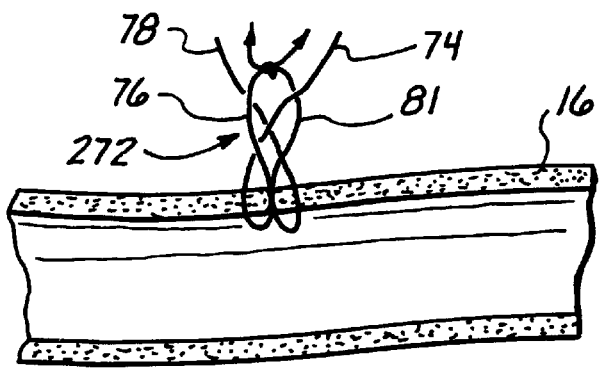
FIG. 55 is a side-elevation view similar to FIG. 54 and illustrating formation of a suture loop.
Figure 57:
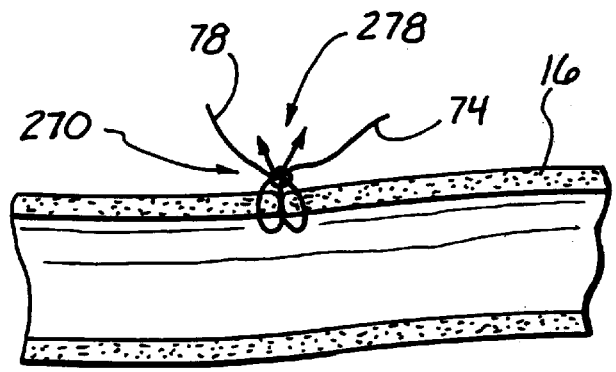
FIG. 57 is a side-elevation view similar to FIG. 53 with a novel suture knot loosely tied to illustrate a figure-eight configuration with portions of the suture extending through the incision to facilitate an abutting relationship between the edges of the incision.

Initially, the suture ends 76, 81 can be tied to form a knot 270 illustrated in FIG. 54. Once this knot 270 is formed, the suture ends 76, 81 form a loop 272 having a first side 274 and a second side 276 best illustrated in the top view FIG. 56. Spreading the loop 272, the suture end 74 can be threaded through the loop 272 from the first side 274, and the suture end 78 can be threaded through the loop 272 from the second side 276. Pulling on the suture ends 74 and 78 will draw the knot 270, loop 272, and suture ends 74, 78 into the incision 12 in a figure-8 configuration. At this point, the suture ends 74 and 78 can be further tied, for example, in a square knot 278.

Figure 8:
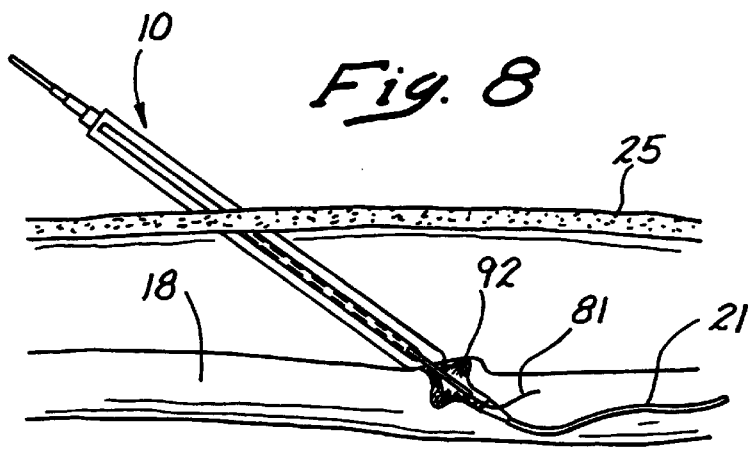

The figure-8 configuration of the resulting suture is illustrated in the axial cross-section view of FIG. 32. From this view it is apparent that the figure-8 configuration of the suture is of particular advantage as it greatly facilitates disposition of the edges of the incision 12 in an abutting relationship. With portions of the sutures 32, 34 passing through the incision 12, the sides of the incision 12 cannot assume either an overlapping relationship or a juxtaposed relationship, which often results from a conventional-loop suture. Once again it will be noted that this highly-advantageous suture structure can be accomplished with the suture apparatus 10 in a totally blind environment and without any access to the far side 30 of the wall 16.

Although several embodiments of the apparatus 10 have been disclosed, along with the associated methods, it will be appreciated that many modifications in these structures and methods will be apparent to those skilled in the art. For example, the mesh disclosed for one embodiment of the expandable structure 92 may be a woven or non-woven material commonly consisting of a multiplicity of fibers which define interstices of the mesh material. In such a structure, it may be that the needles 70, 72 will penetrate the interstices of the mesh so that the capture of the suture ends is somewhat more difficult. In such an embodiment, it may be desirable to coat the mesh material of the expandable structure 92 so that the mesh in the low-profile state firmly captures the suture ends 76, 81. As noted, this capture may occur when the expandable structure 92 is merely returned to its low-profile state. If the capture is sufficient at this point, the entire suture apparatus can be removed, drawing with it the suture ends 76, 81. In embodiments wherein the capture is not sufficiently effected by returning the structure 92 to a low-profile state, it may be further desirable to draw the structure 92 back into the sheath 47 to further compress the structure around the suture ends 76, 81.

It will also be apparent that many of the functions associated with the finger tabs 61, 63, 64, and 65 can be combined. For example, the finger tabs 61 and 65 associated with the needles 70, 72 can be combined into a single tab.

In a further embodiment that single tab might also be combined with the tab 63, which deploys the structure 92 to its high-profile, radially-expanded state. When these three functions are combined in a single finger tab, it is desirable that the initial proximal movement of that tab first deploy the expandable structure 92 and then advance the needles 70, 72. Movement of the single tab in the proximal direction would first retract the needles and then permit the expandable structure 92 to return to the low-profile state. A detent might be provided on such a tab at its most proximal position in order to maintain the suture ends 76, 81 in the captured state during removal of the suture apparatus 10.

The handle assembly 56 can also take many forms. In addition to the form illustrated in FIG. 1, this handle assembly 56 could take the form of a pistol grip or even a scissors-type handle such as that commonly associated with graspers.

Although the foregoing embodiments have each disclosed a two-needle construction, it will be apparent that the suture apparatus 10 can function with more than two needles. In most cases, the total number of needles will be a multiple of two, particularly where the procedure is terminated with a four-end knot of the type disclosed. With multiple-needle embodiments, the needles will typically be arranged in a predetermined pattern. For example, a pattern where associated pairs of the needles are disposed on opposite sides of the wound or incision.

In a particular procedure, it might be desirable to replace the knot with some other type of retention member or device. For example, a crimp ring (not shown) might replace either the knot 130 or the square knot 138 and slid down the associated suture ends 76, 81 and 74, 78, respectively.

It will be understood that many other modifications can be made to the various embodiments of the present invention herein disclosed without departing from the spirit and scope thereof. For example, various sizes of the surgical device, and particularly the outer sheath 47, are contemplated as well as various types of construction materials. Also, various modifications may be made in the configuration of the parts and their interaction. Therefore, the above description should not be construed as limiting the invention, but merely as an exemplification of preferred embodiments thereof. Those of skill in the art will envision other modifications within the scope and spirit of the present invention as defined by the following claims.

What is claimed is:

1. A method for closing an incision defined by surrounding tissue forming a body wall having a near side and a far side, comprising the steps of:

providing a needle having a lumen and being movable along a needle path;

threading a suture having a first end and a second end through the lumen of the needle;

inserting a receiver through the incision from the near side to the far side of the body wall;

expanding the receiver into the path of the needle;

supporting the tissue with the receiver on the far side of the body wall;

moving the needle and the first end of the suture along the path through the surrounding tissue and into the receiver on the far side of the wall;

during the moving step, embedding the first end of the suture in the receiver on the far side of the wall;

capturing the first end of the suture in the receiver to form a removable attachment between the first end of the suture and the receiver;

withdrawing the receiver and the first end of the suture from the far side of the wall through the incision to the near side of the wall; and removing the first end of the suture from the receiver to bring the first end of the suture into proximity with the second end of the suture with the suture extending through the surrounding tissue and the incision.

2. The method recited in claim 1 wherein the inserting step includes the steps of:

providing a guidewire;

positioning the guidewire to extend through the incision; and inserting the receiver over the guidewire and through the incision from the near side of the wall to the far side of the wall.

3. The method recited in claim 1 wherein prior to the moving step the method comprises the step of radially expanding the receiver.

4. The method recited in claim 3 wherein the step of radially expanding the receiver includes the step of radially stretching the receiver.

5. The method recited in claim 3 further comprising the steps of providing the receiver with memory characteristics; and the step of radially expanding the receiver includes the step of permitting the memory characteristics of the receiver to radially expand the receiver.

6. The method recited in claim 1 wherein following the expanding step, the receiver is in an expanded state and the withdrawing step further comprises the step of withdrawing the receiver in the expanded state from the far side of the wall through the incision to the near side of the wall.

* * * * *